US012712053B2

(12) United States Patent
Dittmer et al.

(10) Patent No.: US 12,712,053 B2
(45) Date of Patent: Aug. 18, 2026

(54) DETERMINING THE STABILITY OF A SUBSTANCE OR SUBSTANCE MIXTURE

(71) Applicant: BIONORICA SE, Neumarkt (DE)

(72) Inventors: Martin Dittmer, Neumarkt (DE); Stefan Wiesneth, Regensburg (DE)

(73) Assignee: BIONORICA SE, Neumarkt (DE)

( * ) Notice: Subject to any disclaimer, the term of this patent is extended or adjusted under 35 U.S.C. 154(b) by 0 days.

(21) Appl. No.: 18/826,709

(22) Filed: Sep. 6, 2024

(65) Prior Publication Data

US 2024/0428901 A1 Dec. 26, 2024

Related U.S. Application Data

(63) Continuation of application No. PCT/EP2023/081994, filed on Nov. 16, 2023, which is a continuation of application No. PCT/EP2022/082679, filed on Nov. 21, 2022.

(51) Int. Cl.
*G16C 60/00* (2019.01)
*G16C 20/70* (2019.01)

(52) U.S. Cl.
CPC ............ *G16C 60/00* (2019.02); *G16C 20/70* (2019.02)

(58) Field of Classification Search
CPC ................................ G16C 60/00; G16C 20/70
See application file for complete search history.

(56) References Cited

U.S. PATENT DOCUMENTS

2021/0005287 A1* 1/2021 Fuentes ................ G06T 7/0012
2022/0261510 A1* 8/2022 Takemoto .............. G06F 30/27
2023/0194415 A1* 6/2023 Reimann ............... G16C 20/20 250/252.1
2023/0267369 A1* 8/2023 Kalivas ................. G16B 40/20 706/12

OTHER PUBLICATIONS

Feng, Lei; "Nondestructive Detection of Postharvest Quality of Cherry Tomatoes Using a Portable NIR Spectrometer and Chemometric Algorithms"; Food Analytical Methods, Springer New York LLC, US, Bd. 12, Nr. 4, 8. Jan. 2019 (Year: 2019).*

(Continued)

*Primary Examiner* — Yossef Korang-Beheshti
(74) *Attorney, Agent, or Firm* — Blueshift IP; Robert Plotkin

(57) ABSTRACT

The invention relates to a computer-implemented method for determining the stability of a substance or substance mixture. According to an embodiment, the method comprises the following steps: a data acquisition step in which at least one measurement data record is received, every measurement data record representing a chemical, in particular photochemical profile of the substance or substance mixture in question; a data evaluation step which comprises for each measurement data record: determining an initial value of the material or material mix in question on the basis of the measurement data record; and quantifying the change of the material or material mix in question in relation to the initial value by means of a mathematical distance value; and a data output step in which the change of the material or material mix in question is graphically represented for every measurement data record.

11 Claims, 18 Drawing Sheets

(56) References Cited

OTHER PUBLICATIONS

Alonso-Salces, Rosa M., Margaret V. Holland, and Claude Guillou. "1H-NMR fingerprinting to evaluate the stability of olive oil." Food Control 22.12 (2011): 2041-2046.
Feng, Lei, et al. "Nondestructive detection of postharvest quality of cherry tomatoes using a portable NIR spectrometer and chemometric algorithms." Food Analytical Methods 12 (2019): 914-925.
International Preliminary Report on Patentability issued in App. No. PCT/EP2023/081994, dated Nov. 16, 2023, 26 pages.
Johnston, Carol S., and D. L. Bowling. "Stability of ascorbic acid in commercially available orange juices." Journal of the American Dietetic Association 102.4 (2002): 525-529.
Morozova, Maria, Tatyana Elizarova, and Tatyana Pleteneva. "Discriminant analysis and Mahalanobis distance (NIR diffuse reflectance spectra) in the assessment of drug's batch-to-batch dispersion and quality threshold establishment." European Scientific journal 9.27 (2013).
Peyvasteh, Motahareh, et al. "Meat freshness revealed by visible to near-infrared spectroscopy and principal component analysis." Journal of Physics Communications 4.9 (2020): 095011.
Posada, Huver, et al. "Stability across environments of the coffee variety near infrared spectral signature." Heredity 102.2 (2009): 113-119.
Qin, Yuhua, et al. "Similarity measure method based on spectra subspace and locally linear embedding algorithm." Infrared Physics & Technology 100 (2019): 57-61.

* cited by examiner (A) Pre-test 100
75
50
25
0
Viability [%]
$R^2$=0.955
0.0 2.5 5.0 7.5 10.0
EtOH concentration [%]

(B) Main test 0.24
0.20
0.16
0.12
Euclid. distance
$R^2$=0.999
0 2 4 6
EtOH concentration [%]

(C) Correlation btw. Viability measures

Euclidian distance

LC/MS data, 20% EtOH extract (rosemary, thyme, chamomilla)

Distance

1000

750

500

250

0 1 3 4 6 8 12 24 SunT

Time

Climate zone

KII

AC

B

W

DETERMINING THE STABILITY OF A SUBSTANCE OR SUBSTANCE MIXTURE

TECHNICAL FIELD

The present invention relates generally to the technical field of analytics, in particular pharmaceutical analytics.

BACKGROUND OF THE INVENTION

The development of new products, for example in the pharmaceutical, cosmetic and food sectors, is subject to an ever-increasing catalogue of requirements and strict quality criteria. In such developments, stability studies in particular play a major role, as they are intended to cover a large number of possible influencing factors (e.g. chemical or physical incompatibilities between molecules in a product, resilience with respect to temperature and/or humidity, resistance to UV/VIS radiation, oxidation, interactions between different reactants, microbial attack, biodegradation, etc.).

According to the established approach, the testing of each parameter in a product individually for its reactions to the above-mentioned and other factors can only be characterized by a large number of different technical methods. Typically, several different HPLC methods ("High Performance Liquid Chromatography") are required for different analytes, wet chemical colorimetric group reactions, moisture determination and the testing of physical parameters (e.g. breaking strength, friability and disintegration time of tablets; flowability, bulk and tapped density of powders; turbidity measurements of liquids; and many more).

In order to be able to map as many of such potential interactions as possible, it is common practice to plan the project using a "Design of Experiments" (DoE, synonym: Statistical Experimental Design). This usually takes into account not only all possible qualitative compositions, but also quantitative ratios of the substances contained. In addition, it can also be considered, for example, which packaging material (primary and/or secondary or other packaging material) can best protect a product from changes. Packaging materials are products that are used to package products. Should all these If aspects are also integrated into a test plan, the number of product variants is multiplied again by the packaging options to be tested.

A distinction is generally made between primary packaging and secondary packaging. Primary packaging for medicinal products and medical devices includes containers or Components made of glass, rubber, plastic, aluminum and composite materials as well as films. These materials come into direct contact with the medical products and must therefore meet certain requirements regarding safety, effectiveness and reliability. Manufacturers of primary packaging materials must meet the expectations of pharmaceutical manufacturers and be able to demonstrate that their production processes are subject to an integrated quality management system (QMS) and the rules of Good Manufacturing Practice (GMP) and thus meet the required quality standards. Secondary packaging is understood to be outer packaging that is not in direct contact with the objects to be packaged. Medicines or other substances and which usually have a protective and control function.

This results in a project design with a large number of samples coupled with numerous analysis methods, which ideally would have to be carried out seamlessly for all samples. However, since an enormous gain in information is to be expected from such experimental designs, it is desirable to carry them out in order to ultimately determine the best possible product with the longest product lifespan. This is offset by the need for a very large amount of personnel and equipment that would be required for implementation using classical analytical methods. With the established staff and equipment fleet, such a comprehensive investigation could only be carried out with great difficulty, as the required working time and financial investment would hardly be acceptable, and timelines for such product developments would be massively extended. The alternative would be a drastic reduction in measurement effort, which could, however, lead to unacceptable product quality.

In addition to the enormous effort required to collect a comprehensive data set as part of a stability study, the interpretation of such a huge data set also represents a major challenge. This is due to the fact that in the "classical" consideration of the original data, in which often only a small subset of the total data is evaluated (for example, considering only the three strongest signals of an HPLC chromatogram instead of considering the complete "fingerprint area"), a weak trend or an anomaly may be masked or not recorded at all. Modern chemometric methods can help here. methods provide. These include, for example, principal component analysis, correlation analysis, distance measures, partial least squares regression, support vector machines, and neural networks. Such methods are able to convert a complex original data set with numerous variables (here: test parameters) into a few latent variables that are still able to describe the data set with sufficient accuracy.

Therefore, the implementation of chemometric methods for simple and efficient evaluation of a data set is essential to solve the problem. Due to the personnel, financial and time-related aspects mentioned above, products are currently only tested for stability with regard to a few parameters. This results in certain other unmeasured parameters that may affect stability either not being found and thus may result in an inferior product. It is therefore of immense advantage to record the stability properties of a product as a whole and not on the basis of individually selected parameters that determine the stability of a substance or mixture of substances from which the product or, for example, is made. B. its packaging, may not be reflected correctly in its entirety. Important parameters could be ignored and lead to suboptimal products. The present invention solves these problems by improving the properties of a product or service. substance or mixture of substances (hereinafter "mixture of substances") in its entirety and enables a concrete statement to be made regarding the stability of the entire product. The analysis of a large number of parameters is therefore no longer necessary due to the present invention.

It is therefore an object of the present invention to provide a method for determining the stability of a mixture of substances, with which the above-mentioned disadvantages of the prior art can be overcome. Furthermore, the calculation method can also be used to monitor processes in which a large number of monitoring parameters are recorded in parallel.

DESCRIPTION

The present invention comprises a computer-implemented method for determining the stability of a mixture of substances, as well as for monitoring processes in which a large number of monitoring parameters are recorded in parallel. The method comprises at least a data acquisition step in which at least one measurement data set is received, as well as at least one subsequent data acquisition step in which at least one further measurement data set is received.

The first data acquisition step comprises the at least one starting value measurement data set. Each measurement data set can provide a chemical, especially phytochemical, profile of a particular mixture of substances represent. The method may further comprise a data evaluation step. An evaluation is the processing of (raw) data from an experiment with the (raw) data from the at least one starting value measurement data set and the at least one further measurement data set to generate concrete knowledge. The data evaluation step comprises, for each measurement data set, determining a starting value of the respective substance mixture on the basis of the measurement data set. Furthermore, the data evaluation step comprises quantifying the change of the respective substance mixture with respect to the starting value by means of a mathematical distance measure by determining at least one further subsequent data acquisition step with the at least one further measurement data set. The method may further comprise a data output step in which the change in the respective substance mixture is graphically displayed for each measurement data set.

A mixture of substances according to the present invention comprises both individual substances and combinations or mixtures of substances as well as chemical and/or biological products. The terms "substance or mixture of substances", "combination" and "product" are understood as equivalent terms in the context of the present invention.

The stability of a substance mixture within the meaning of the present invention is understood as a measure of the period of time during which the change in the respective substance mixture remains within previously defined limit values. This includes in particular chemical and/or physical stability. Within the framework of a stability study, the stability can be investigated according to the method according to the invention. A stability study is therefore understood as an experiment that investigates whether different mixtures of substances are stable at all or how quickly their stability decreases. Alternatively or additionally, it may be provided that, within the framework of such an investigation, different mixtures of substances, in particular formulations, are compared with each other. The stability includes the change in a substance over a period of time that is measured between at least two points in time. The first time point comprises the first data acquisition step with the at least one starting value measurement data set, the second comprises the second and all further data acquisition steps with the at least one further measurement data set.

Furthermore, this method can also be used to monitor production processes or reactions (see application example 3). These include chemical or biological production processes and reactions, such as extractions, tabletting, capsule filling, mixing processes. For example, the novel method can be used to monitor equilibrium in an extraction process without prior calibration of a method and to determine the time at which equilibrium is reached. In the present method, the equilibrium setting is indicated by asymptotic approximation of the calculated distance values to a plateau as shown in FIGS. 8 and 9.

A chemical profile of a mixture of substances is defined as the totality of the chemical compounds of the mixture and/or the chemical properties or reactivity of the mixture of substances. A phytochemical profile of a mixture of substances is understood as the totality of the chemical compounds of the mixture originating from plant components and/or the properties of the mixture resulting from them.

The challenges and requirements described above define the criteria that a novel analytical concept must fulfill. The method according to the invention enables a rapid and comprehensive investigation of mixtures of substances prepared in parallel and their comparison with each other, even over a period of time. This advantageously enables a relative comparison of product variants in order to select a selection of promising candidates, for example in the context of drug research.

For the purposes of the present disclosure, a medicinal product is understood to mean: a) All substances or compositions of substances/mixtures which have properties for curing or preventing human diseases or diseases, or (b) any substance or combination of substances/mixtures intended for use in or on the human or animal body or intended to be administered to a human or animal for the purpose of restoring, correcting or modifying human or animal physiological functions by a pharmacological, immunological or metabolic action or to make a medical diagnosis.

A particular advantage underlying the method according to the invention is that a significantly reduced selection of possible product candidates can be generated with very little effort during product development, so that subsequently, for example, only these product candidates have to be further investigated using other specific classical analytical methods. By concentrating on certain promising product candidates, further detailed knowledge can be efficiently obtained to enable a final selection of the best product variant. In particular, the proposed method according to the invention can make it possible to carry out analytical processing of large-scale product comparisons with very low personnel and equipment capacities in a reasonable time. The process according to the invention is particularly advantageous for complex mixtures of substances, but can also be used for products with few individual components and individual compounds. The method according to the invention makes it possible, through a comprehensive evaluation of complex measurement data sets which represent the most comprehensive possible (phyto-) chemical profile of all samples of a stability study, to identify those substance mixtures which show the smallest change in relation to their starting value and the smallest variance and can thus be assumed to be the most stable.

Preferably, the method, in particular the data evaluation step, comprises the use of a machine learning model, which was preferably generated or trained by unsupervised and/or supervised machine learning. Unsupervised machine learning is a mathematical or information technology process in which a data processing device/computer processes data without additional external information and tries to find a solution independently. An example of this is the "principal component analysis". Supervised machine learning is a mathematical or information technology procedure in which a data processing device/computer processes data with the help of external information (e.g. training data, in particular information about concentrations used in an experiment). An independent search for a solution typically takes place after calibration on already known data.

It is particularly preferred that the at least one measurement data set comprises data obtained by means of near-infrared spectroscopy.

Near-infrared spectroscopy (NIR) can be used to measure samples of mixtures of substances without complicated sample processing and in a non-destructive manner in order to generate measurement data sets. Near-infrared spectroscopy, abbreviated to NIR spectroscopy or NIRS, is a physical analysis technique based on spectroscopy in the range of short-wave infrared light. In NIRS, detection takes place in the near infrared, preferably from approx. 760-2500 nm (equivalent to approx. 13160 $cm^{-1}$ to 4000 $cm^{-1}$). This technology detects combination and overtone vibrations of all molecules in a sample and is therefore able to capture them holistically. In order to evaluate this data, mathematical methods (chemometrics) are used in particular, since the information contained in these spectra (e.g. presence/absence of certain chemical compounds, concentrations, etc.) would otherwise usually remain hidden from the observer. Near-infrared spectroscopy can be used advantageously for liquid samples (e.g. measurement of transmission, i.e. the measuring beam passes through the sample in a defined layer thickness and the non-absorbed Light is detected by a detector or transflectance, i.e. the measuring beam hits the sample. The reflected light is detected by a detector. The absorption indicates the difference between incident and reflected light) as well as for solid samples (measurement of diffuse reflection or transmission, for example).

One aspect of the method according to the invention is to provide a machine-based and machine-reproducible data evaluation of measurement data sets. The advantage of data sets obtained, for example, using near-infrared spectroscopy (NIR) is that these data sets contain much more information in one observation date compared to data sets obtained from other analytical techniques, because classical analytical techniques only observe a few isolated signals at the same time. Near-infrared spectroscopy enables a broader evaluation of a variety of signals.

Preferably, the at least one measurement data set additionally or alternatively comprises: data obtained by means of UV/VIS spectroscopy, data obtained by means of Raman spectroscopy, a (U) HPLC fingerprint, a GC fingerprint, a peak table from a chromatographic process, and/or at least one physical, biological or chemical parameter, in particular sugar content, disintegration rate, color, breaking strength, disintegration time, friability, density, viscosity, refractive index and/or optical rotation angle.

UV/VIS photometry is a spectroscopic method belonging to optical molecular spectroscopy that uses electromagnetic waves of ultraviolet (UV) and visible (VIS) light, whereby a light source emits ultraviolet and visible light in the wavelength range from about 200 nm to about 800 nm.

In Raman spectroscopy, the material to be examined is irradiated with monochromatic light, preferably with a laser. In the spectrum of the light scattered by the sample, additional frequencies are observed in addition to the incident frequency (Rayleigh scattering). The frequency differences to the incident light correspond to the energies of rotational, vibrational, phonon or spin-flip processes characteristic of the material. From the spectrum obtained, conclusions can be drawn about the substance under investigation.

(U)HPLC ((Ultra) high performance liquid chromatography) is a standard analytical method (liquid chromatography process) that can not only separate substances, but also identify and quantify them using standards. Non-volatile substances can also be analyzed using (U) HPLC. This can be sent to a sensitive detector system such as mass spectrometry (MS or together IIHPLC MS/MS) can be connected.

As part of the analyses, it is possible to record the complete results as a pattern ("fingerprint"). These fingerprints can be compared with those in a database or with results from other analyses using the same method to identify the substance being analyzed.

The method according to the invention advantageously makes it possible to combine different analytical data sets and incorporate them into an evaluation. For example, the at least one measurement data set for a substance mixture can include data sets that were created using UV/VIS spectroscopy, Raman spectroscopy, (U) HPLC fingerprints (in particular from a coupling with different detectors, for example diode array detector (DAD), refractive index detector, electrochemical detector, UV/VIS detector, MS, light scattering detector (ELSD, engl. Evaporative Light Scattering Detector), GC fingerprints (especially from a coupling with various detectors, for example flame ionization detector (FID), MS) or, more generally, peak tables from all conceivable chromatographic methods. In other words, the method according to the invention can be applied to a variety of measurement techniques that assign one or more X values (e.g. wavelengths, m/z ratios (mass/charge ratio), retention times, measurement points) to one or more Y values (e.g. intensities, absorptions, voltages, measured values). The process is therefore particularly versatile and flexible.

In addition, multidimensional data sets can also be processed using appropriate analytical methods (e.g. HPLC-DAD, HPLC-MS). Furthermore, large data matrices from individually collected test parameters (i.e. also using different techniques) (for example physical, biological or chemical analyses (but not limited to these)) can be combined for evaluation and subjected to the new procedure. For example, the measurement of the sugar content, the disintegration rate, the color of the tablet and the breaking strength could be compiled into a data matrix and evaluated from a data set that was measured over several points in time.

It may also be provided that the quantification of the change in the respective mixture of substances is based on the totality of the ingredients of the respective mixture of substances. By taking into account all the ingredients of a mixture of substances to be examined, it is particularly easy to generate reliable results. In particular, all spectral changes of all ingredients in relation to a starting value are taken into account in a stability study. In contrast to classical marker analysis (e.g. using HPLC), this enables a holistic examination of all ingredients of complex mixtures (e.g. using near-infrared spectroscopy), which depicts the fundamental change in the entire sample.

The change in the mixture of substances can be calculated by using a mathematical distance measure.

Preferably, the mathematical distance measure is selected from the following group: Euclidean distance, Mahalanobis distance, Manhattan distance, Pearson distance and/or Gower distance.

By selecting a mathematical distance measure from the group mentioned above, it is ensured that the change in a mixture of substances under investigation is quantified over time, whereby the complexity of the underlying data sets can be processed holistically. The choice of a suitable mathematical strategy to quantify the degree of change of a sample over time thus enables an efficient quantification of the change of a particular mixture of substances. In particular, a very good comparative overview of a data set from a stability study is obtained without having to check a large number of separate parameters individually.

It is particularly advantageous that the mathematical distance measure can be selected by a user.

The possibility for a user to choose a mathematical distance measure makes the method according to the invention more flexible and adaptable. In particular, a user can incorporate his experience in order to select a suitable mathematical distance measure in order to determine the stability of a substance mixture using the method according to the invention.

In particular, it can be provided that the user also iteratively selects several mathematical distance measures one after the other for the quantification of the change in the respective substance mixture, whereby the quantification is carried out on the basis of each selected mathematical distance measure. This allows a user to compare results of different selectable mathematical distance measures. This makes the method for determining the stability of a mixture of substances particularly flexible and versatile. By providing this possibility, an unintentional selection of a mathematical distance measure for quantifying a change in respective mixtures of substances can also be changed.

Preferably, the method further comprises a data preprocessing step. This may comprise performing a stray light correction of the at least one measurement data set, in particular if it comprises near-infrared measurement data. Furthermore, the data preprocessing step may comprise performing a centering, normalization and/or scaling of the at least one measurement data set. Furthermore, the data preprocessing step may also include performing a principal component analysis.

Data preprocessing is understood here as the mathematical processing of raw data with the aim of preparing the actual evaluation. This can, for example, be a stray light correction, an increase in the signal-to-noise ratio or a simple reformatting of recorded measurement data sets. Include raw data so that the data fed in during a subsequent evaluation can be correctly processed by the algorithm. Suitable data preprocessing can be used in particular to increase the quality of the results of the method according to the invention. The data preprocessing preferably takes place after the data acquisition step of the method according to the invention.

Through appropriate data preprocessing, which may in particular include a reduction in the amount of data, possible parameter interactions within a complex overall data set should be automatically recorded and taken into account. In other words: The accuracy of the method according to the invention or the evaluation quality can be increased by carrying out a stray light correction (for example in the case of near-infrared spectroscopy data), in particular before the actual data evaluation.

Normalization or scaling of the data, as well as a prior principal component analysis, can also separate unwanted noise from the information in a data set and thus further increase the quality, validity and robustness of the data. Noise is understood to be a disturbance with a broad, unspecific frequency spectrum, which can possibly overlay or mask desired, information-bearing signals. An example of noise is unwanted scattered light, which in addition to desired excitation light falls randomly on the detector of a near-infrared spectroscopy device and is additionally measured. The application of special mathematical techniques can help to separate noise from usable information, thus increasing the signal-to-noise ratio and making an evaluation more robust/trustworthy.

It can further be provided that the data output step comprises: displaying the change in the respective substance mixture as a box plot; and/or displaying mean values, medians, 0.25/0.75 quantiles, highlighting possible outlier candidates; and/or carrying out at least one statistical test, in particular t-test, Wilcoxon rank sum test, one-way ANOVA and/or Kruskall-Wallis test.

This design of the data output step enables the examination of very large measurement data sets, especially with a large number of samples, with greater significance and at the same time less time expenditure. Furthermore, an intuitive evaluation is advantageously provided. This means that this technology can be used by users without in-depth mathematical knowledge and no individual programming is required for each examination. A user can gain insights at a glance and in a simple, intuitive way, for example in a data output step that outputs the change in the substance mixture under investigation as a box plot. Highlighting means, medians, 0.25/0.75 quantiles and outliers further increases user-friendliness. Measurement data sets collected by a user can, for example, be fed into the process directly from a measuring device or after a data preprocessing step, as described above, and an easily interpretable evaluation is immediately generated.

It can further be provided that the determination of the starting value of the respective substance mixture is based on metadata of the respective measurement data set.

By using metadata when determining the starting value, examination time and/or processing time can be saved. The starting value is determined in a short time based on metadata.

Preferably, the data evaluation step further comprises: performing an additional principal component analysis for the measurement data set, which is not included in the quantification of the change by means of the mathematical distance measure, wherein the result of the additional principal component analysis is presented in the data output step.

The additional principal component analysis, which is in particular a qualitative analysis that is not included in the distance calculation, can support the evaluation of output results after the data output step by the user. Through the data output step, the user thus receives, on the one hand, a quantitative analysis, which in particular includes the distance measure, and, on the other hand, a qualitative analysis, which enables further conclusions to be drawn at a glance and in an intuitive manner.

In particular, it can be provided that the mixture of substances comprises solid and/or liquid and/or gaseous mixtures of substances.

It can further be provided that the mixture of substances contains biological, chemical, plant, animal, human substances or mixtures of substances, pharmaceutical compositions, herbal medicinal products, chemical and/or biological medicinal products, cells, cell therapeutics (for example gene therapeutics, e.g. CAR T cells (chimeric antigen receptor T cells), NK cells (natural killer cells), somatic cell therapeutics, biotechnologically processed tissue products/ tissue engineered products, tissue, stem cells, stem cell products or preparations, e.g. CD34+ cells, CD19+ cells, CD20+ cells, HEK295 cells, TCR alpha/beta cells, TCR gamma/delta cells, CD3+, CD4+, CD8+, CD133+ cells), blood, blood products, organs, medicinal teas, extracts, in particular verbena extract, drops, tablets, dragees, capsules, powders, granules, solutions, suspensions, juices, foodstuffs, in particular meat or minced meat, fruit juice, in particular orange juice, food supplements, cosmetics, emulsions, ointments and/or creams, as well as packaging, packaging materials, films, in particular polyethylene, polyvinyl chloride, etc.

The method for determining the stability of a mixture of substances is very versatile. In this way, mixtures of substances in any state of aggregation can be advantageously examined.

The computer program according to the invention comprises instructions which, when the program is executed by a computer, cause the computer to carry out the method as described above.

The device according to the invention can in particular be a measuring instrument or a server computer and comprises means for carrying out the method as described above. The device according to the invention also includes a mobile electronic device, such as a smartphone, a programmable logic device Control or a so-called "Edge device", conceivable. In addition, the process can also be provided as a cloud solution within the framework of "software-as-a-service" or generally as a "serverless" application.

The technical advantages and embodiments described with respect to the method according to the invention apply equally to the computer program according to the invention and to the device according to the invention.

BRIEF DESCRIPTION OF THE DRAWINGS

Preferred embodiments of the present disclosure are described below with reference to the following drawings.

DETAILED DESCRIPTION

Figure 1:
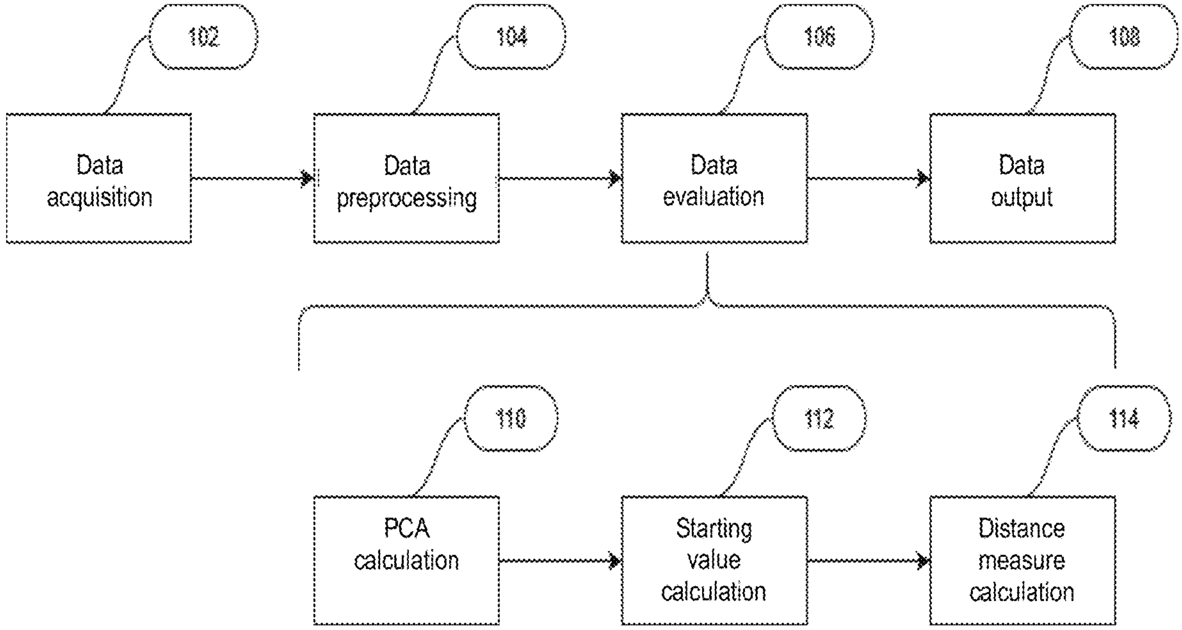
FIG. 1 shows schematically a rough overview of possible steps of the method according to embodiments of the invention.

As shown in FIG. 1, data collection 102 first takes place. At least one measurement data set is received, which can be generated by a measurement using one or more measuring devices. Each measurement data set includes a chemical, particularly phytochemical, profile of the substance mixture to be investigated. The measurement data set or the multiple measurement data sets may in particular comprise data obtained by means of near-infrared spectroscopy. Near-infrared spectroscopy (NIR) can be used to measure samples of substances or mixtures of substances without complicated sample processing in order to generate measurement data sets. This technology detects combination and overtone vibrations of all molecules in a sample and is therefore able to capture them holistically. The advantage of data sets obtained, for example, using near-infrared spectroscopy (NIR) is that these data sets contain much more information in one observation date compared to data sets obtained from other analytical techniques, because classical analytical techniques only observe a few isolated signals at the same time. In other words, near-infrared spectroscopy enables a broader evaluation of a variety of signals. Alternatively or additionally, the measurement data set or the multiple measurement data sets can include data that were recorded by means of UV/VIS spectroscopy, Raman spectroscopy, (U) HPLC fingerprints (in particular from a coupling with different detectors, for example DAD, MS, ELSD), GC fingerprints (in particular from a coupling with various detectors, for example FID, MS) or, quite generally, peak tables from all conceivable chromatographic methods. In other words, the method can be applied to a variety of measurement techniques that assign one or more X values (e.g. wavelengths, m/z ratios, retention times, measurement points) to one or more Y values (e.g. intensities, absorptions, voltages, measured values). The process is therefore particularly versatile and flexible.

In a further, optional step, data preprocessing 104 can take place. This can in particular include: carrying out a stray light correction of the at least one measurement data set, in particular if this comprises near-infrared measurement data; carrying out a centering, normalization and/or scaling of the at least one measurement data set; and/or carrying out a principal component analysis. Suitable data preprocessing can be used in particular to increase the quality of the results of the method according to the invention. Through data preprocessing, which can in particular include a reduction in the amount of data, possible parameter interactions within a complex overall data set are to be automatically recorded and taken into account. In other words, the accuracy of the method according to the invention or the evaluation quality can be increased by carrying out a stray light correction (for example in the case of near-infrared spectroscopy data), in particular before the actual data evaluation.

In a further step, a data evaluation 106 is carried out for each measurement data set. A start value calculation 112 and a distance measurement calculation 114 are carried out for each measurement data set. In the initial value calculation 112, a starting value is determined on the basis of the measured data, from which a change in the substance mixture to be examined is observed and quantified within the framework of the distance measure calculation 114. The distance measure calculation 114 can in particular be carried out on the totality of the ingredients of the substance mixture to be examined in order to increase the robustness and validity of the result.

The distance measure in the distance measure calculation 114 can in particular be selected from the following group: Euclidean distance, Mahalanobis distance, Manhattan distance, Pearson distance and/or Gower distance. Selecting a mathematical distance measure from the above-mentioned group ensures that the change in a substance or mixture of substances under investigation is quantified over time, whereby the complexity of the underlying data sets can be processed holistically. The choice of a suitable mathematical strategy to quantify the degree of change in a sample over time thus enables an efficient quantification of the change in a particular substance or mixture of substances. In particular, a very good comparative overview of a data set from a stability study is obtained without having to check a large number of separate parameters individually.

It is particularly advantageous that the mathematical distance measure can be selected by a user.

The possibility for a user to choose a mathematical distance measure makes the method according to the invention more flexible and adaptable. In particular, a user can incorporate his experience in order to select a suitable mathematical distance measure in order to determine the stability of a substance or mixture of substances using the method according to the invention.

In particular, it can be provided that the user selects several mathematical distance measures for quantifying the change in the respective substance or mixture of substances, whereby the quantification is carried out on the basis of each selected mathematical distance measure. This allows a user to compare the results of different selectable mathematical distance measures.

Alternatively or additionally, the user may select different mathematical distance measures one after the other to quantify the change in the respective substances or mixtures of substances. This makes the method for determining the stability of a substance or mixture of substances particularly flexible and versatile. By providing this possibility, an unintentional selection of a mathematical distance measure for quantifying a change in respective substances or mixtures of substances can also be changed.

Optionally, a PCA calculation 110 can be carried out as part of the data evaluation 106, which precedes the start value calculation 112 and the distance measurement calculation 114. The abbreviation PCA stands for Principal Component Analysis. The data evaluation 106 can thus be carried out both with the original data and after data scaling and/or data reduction to latent variables, for example by the PCA calculation 110. In a final step shown in FIG. 1, the data output 108 takes place. The change in the respective mixture of substances is shown graphically for each measurement data set. The data output 108 can in particular include: displaying the change in the respective substance mixture as a box plot; and/or displaying mean values, medians, 0.25/0.75 quantiles, highlighting possible outlier candidates; and/or carrying out at least one statistical test, in particular t-test, Wilcoxon rank sum test, one-way ANOVA and/or Kruskall-Wallis test. This design of the data output 108 enables the examination of very large measurement data sets, especially with a plurality of samples, with greater significance and at the same time less time expenditure. Furthermore, an intuitive evaluation is advantageously provided. This means that this technology can be used by users without in-depth mathematical knowledge and no individual programming is required for each examination. A user can gain insights at a glance and in a simple, intuitive way, for example in a data output step that outputs the change in the substance mixture under investigation as a box plot. Highlighting means, medians, 0.25/0.75 quantiles and outliers further increases user-friendliness. Measurement data sets collected by a user can, for example, be fed into the process directly from a measuring device or after a data preprocessing step, as described above, and an easily interpretable evaluation is immediately generated.

Figure 2:
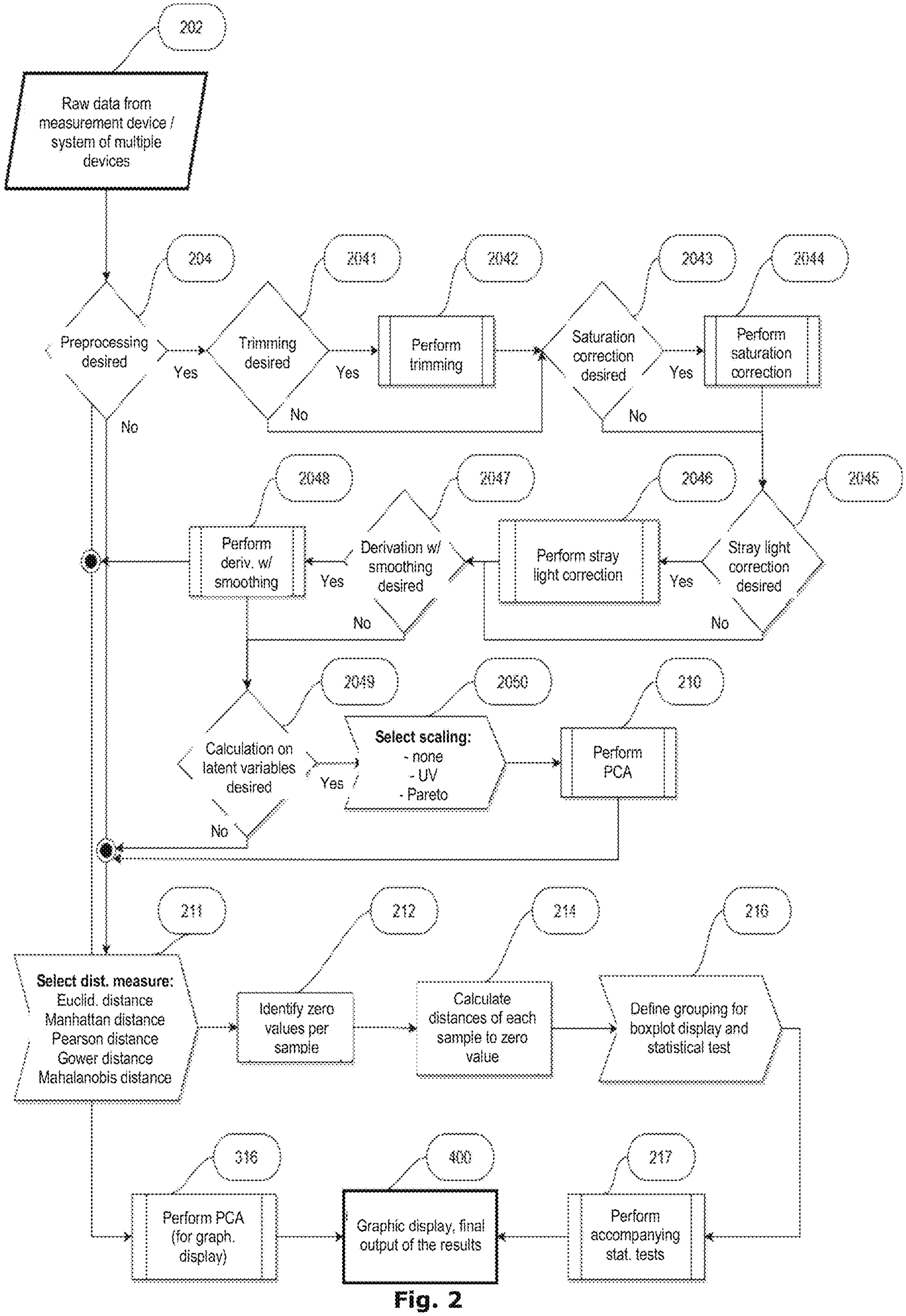
FIG. 2 shows a schematic overview of possible steps of the method according to embodiments of the invention.
Figure 3:
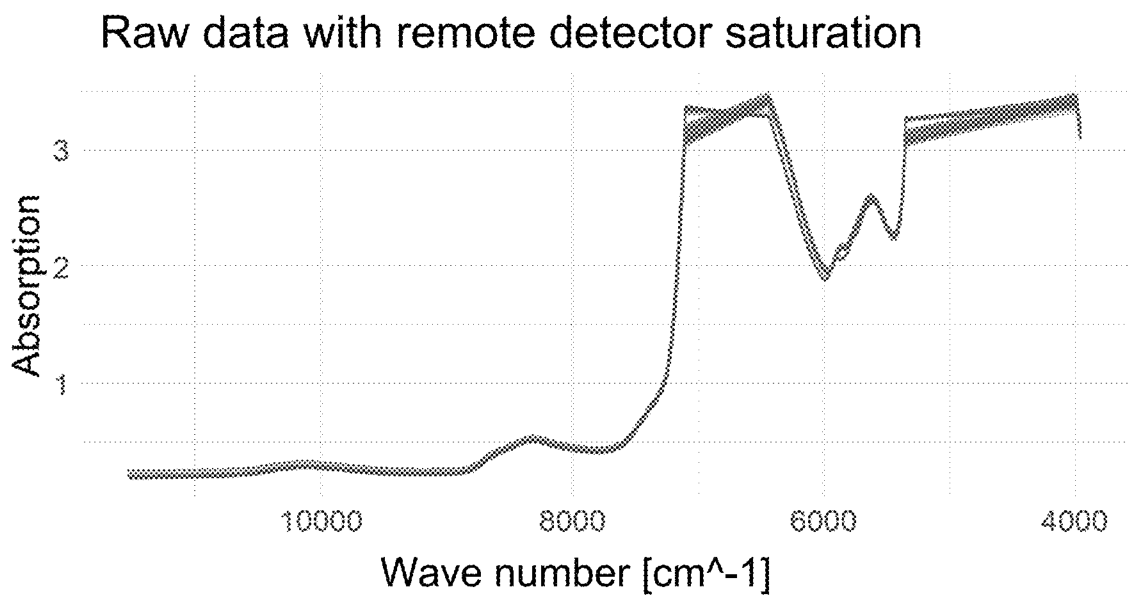
FIG. 3 shows a spectral overlay of measured data sets of a near-infrared spectroscopy device with remote detector saturation.

FIG. 2 shows a schematic overview of possible steps of the method according to embodiments of the invention. The present invention is explained below with reference to FIG. 2.

In a step 202, raw data from one or more measuring devices are compiled. As described above, different measurements of the same mixture of substances or different samples of a mixture of substances can be carried out to collect the raw data (data collection step).

In a step 204, it must be decided whether preprocessing is desired or not. If no preprocessing is desired, the distance measure is selected in a next step 211. The distance measurement can be chosen from the distance measurements mentioned above. After the distance measure has been chosen, a quantitative and/or qualitative evaluation is carried out-depending on the design of the procedure. As part of the quantitative evaluation, initial values or starting values are determined for each measurement data set in a step 212. Zero values identified. In a further step 214, the change in a parameter to be examined is determined, for example over time. mixture of substances is determined using the selected distance measure. The result is grouped and displayed in a step 216, for example in a box plot. In addition, accompanying statistical tests can be carried out in a step 217 as part of the quantitative evaluation. Within the framework of a possible qualitative evaluation 316, for example through an additional principal component analysis, a user can obtain a useful statement in addition to the quantitative evaluation. In a step 400, the results or Results are displayed and output graphically.

If it is decided in step 204 that data preprocessing is desired, a decision is first made in step 2041 as to whether a trimming of the measurement data sets is desired. If a trimming of the measurement data sets is desired, this is carried out in a step 2042. It must then be decided in a step 2043 whether a saturation correction is desired, and if a saturation correction is desired, this is carried out in a step 2044. Furthermore, in a step 2045 it is decided whether a stray light correction is desired. If stray light correction is desired in step 2045, this is carried out in step 2046. Subsequently, in a step 2047, it is decided whether a derivation with a smoothing of the measurement data sets is desired, and if such a derivation is desired, this is carried out in a step 2048. Furthermore, in a step 2049 it is decided whether a calculation on latent variables is desired and a scaling is selected in a step 2050. The scaling can be chosen from "none", "UV" (—'univariance', not to be confused with "ultraviolet")" or "Pareto". It goes without saying that during the optional preprocessing only a selection of the measures described above can be carried out.

In a step 210, a PCA calculation can then be carried out. Then, as described above, we proceed with the selection of the distance measure.

Implementation Example

The experiments described below were carried out using a reference implementation in the R programming language. The reference implementation includes the following steps:

Calculation of the distances of the individual observations/samples using suitable distance measures (e.g. Euclid, Mahalanobis, Manhattan, Pearson, Gower, or similar) to their starting value ("zero month value"). This distance calculation can be performed on raw data as well as on the latent variables of a preprocessing (e.g. PCA, data scaling, etc.). From the calculated Distance measurements also make it possible to determine the kinetics of the degradation of a product. In this way, for example, half-lives can also be used to identify the most stable variant(s).

Easy-to-interpret representation of the calculated distances in box plots including automatic execution of descriptive statistics (calculation and representation of means, medians, representation of the 0.25/0.75 quantiles, drawing of possible outlier candidates) and defining/executing the most suitable statistical test (t-test/Wilcoxon rank sum test/one-way ANOVA/Kruskall-Wallis test) to compare the means.

Ability to track changes in samples over time including estimation of statistical significance (e.g. whether further degradation occurs in the samples after n months or whether a plateau has been reached)

Converting the spectral data into latent variables using principal component analysis (PCA) in order to additionally estimate different types of degradation or rearrangement mechanisms via score plots. Two cases can be distinguished here:

A) A PCA can be calculated from the raw data, the score values of which are then used in the distance calculation and later boxplot representation & statistics. These scores are then also displayed graphically.

B) The actual distance calculation (and boxplot representation, as well as the associated statistics) can also be carried out without a preceding PCA—this is then still calculated and displayed, but is not included in the actually critical distance calculation.

The created app enables intuitive evaluation without programming or in-depth mathematical knowledge for the end user.

The corresponding calculation method of the implementation in an embodiment of the invention is described below:

The starting point in this embodiment is a raw data table prepared by the user, which contains the samples to be examined and meta-information (for example, in which climate zone or in which month the sample was measured). Each row is a sample, each column is a "property", for example intensity at a measured wavelength or numerical value of the breaking strength, concentration of a contained substance or other measured parameters. The number of columns may vary depending on the measurement method and the availability/relevance of additional meta-information. An excerpt from an example raw data table is shown here:

TABLE 1

Example excerpt from the raw data set for application example 1. This includes both the meta-information and the NIR spectra at different times under different climatic conditions regarding a stability study on orange juice.

| Meta information | | | Wave number [cm$^1$] | | |
|---|---|---|---|---|---|
| Product | Time (in days) | Climate | | | |
| | | | 11544 | . . . further wave numbers . . . | 3952 |
| Orange juice | 0 | sw | 2,4833 | . . . further intensity values . . . | 4,61342 |
| Orange juice | 0 | sw | 2,51817 | . . . further intensity values . . . | 4,38362 |
| Orange juice | 1 | 40° C. | 2,56125 | . . . further intensity values . . . | 4,68658 |
| Orange juice | 1 | 40° C. | 2,576 | . . . further intensity values . . . | 4,77443 |
| Orange juice | 1 | RT | 2,52725 | . . . further intensity values . . . | 4,41684 |
| Orange juice | 1 | RT | 2,5428 | . . . further intensity values . . . | 4,78359 |
| Orange juice | 2 | 40° C. | 2,62842 | . . . further intensity values . . . | 4,44054 |
| Orange juice | 2 | 40° C. | 2,54003 | . . . further intensity values . . . | 4,39748 |
| Orange juice | 2 | RT | 2,61846 | . . . further intensity values . . . | 4,66339 |
| Orange juice | 2 | RT | 2,57705 | . . . further intensity values . . . | 4,59864 |
| Orange juice | 3 | 40° C. | 2,58429 | . . . further intensity values . . . | 4,44866 |
| Orange juice | 3 | 40° C. | 2,57807 | . . . further intensity values . . . | 4,70549 |
| Orange juice | 3 | RT | 2,59324 | . . . further intensity values . . . | 4,42383 |
| Orange juice | 3 | RT | 2,59459 | . . . further intensity values . . . | 4,8207 |
| Orange juice | 4 | 40° C. | 2,61964 | . . . further intensity values . . . | 4,77069 |
| Orange juice | 4 | 40° C. | 2,64142 | . . . further intensity values . . . | 4,46515 |
| Orange juice | 4 | RT | 2,57869 | . . . further intensity values . . . | 4,35357 |
| Orange juice | 4 | RT | 2,6016 | . . . further intensity values . . . | 4,35946 |

Especially with NIR spectra, it may be desirable to use only certain wavenumber ranges for the evaluation, so that these can be cut out and reassembled if desired.

In the case of NIR spectra, it can happen during the measurement process that the sensitivity of the detector is exceeded in certain wavenumber ranges (for example, in 5 the case of aqueous samples in the range of approx. 5400 $cm^{-1}$ to 4900 $cm^{-1}$, which reacts very sensitively to water contained in the sample). Since detector saturation does not contain any relevant information and could compromise the evaluation quality, such areas can be deliberately cut out and excluded from further analysis if desired.

In NIR spectra, a baseline shift may occur in individual spectra if unwanted scattered light occurred during the measurement. This can be remedied by a stray light correction. One possibility is the so-called Vector normalization (SNV normalization), which works as follows: A sample matrix P is first transposed, then the corrected value is calculated for each value per column according to the formula $$x' = \frac{x - \bar{x}}{\sigma}.$$

Figure 4:
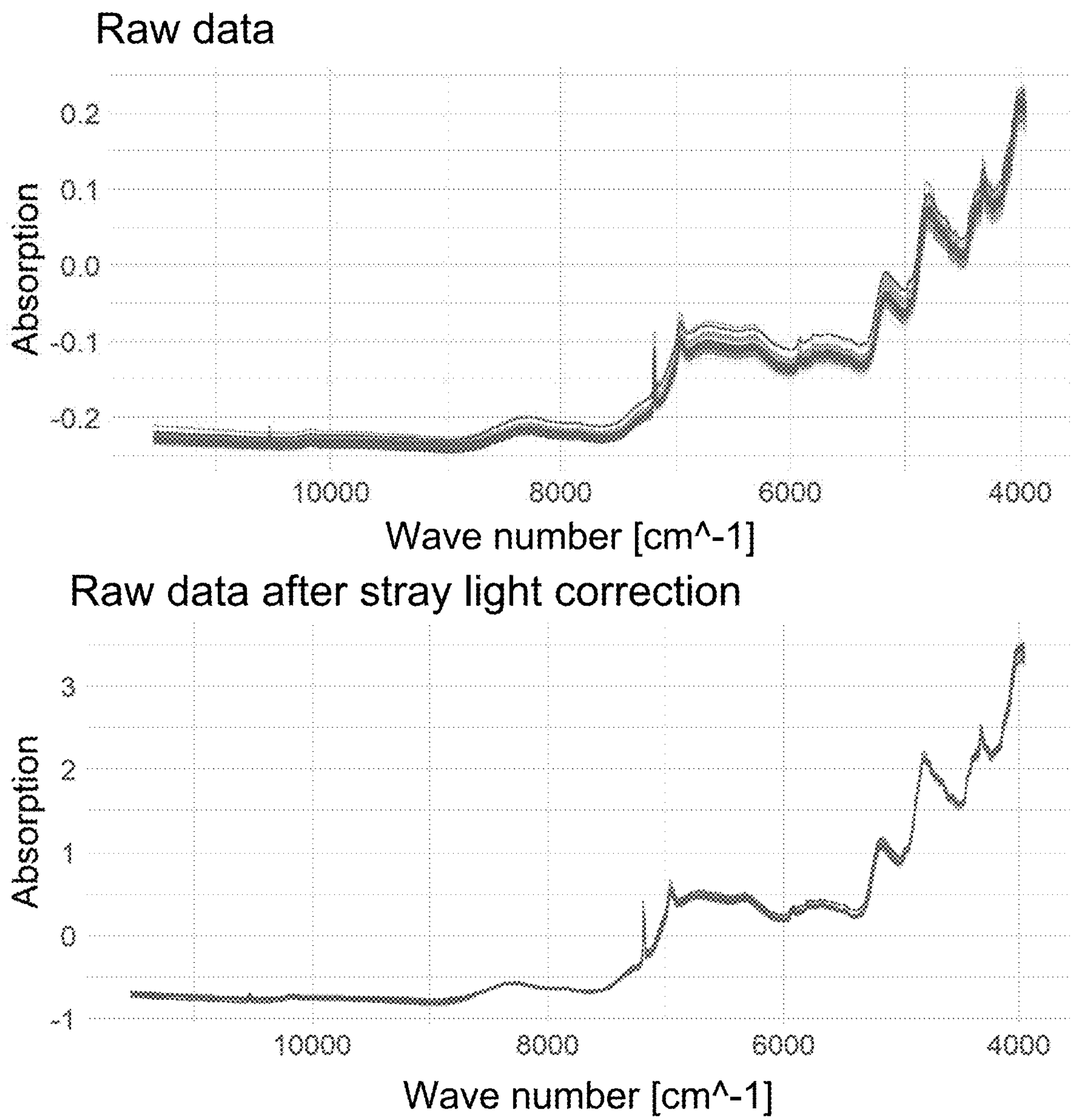
FIG. 4 shows a spectral overlay of measured data sets of a near-infrared spectroscopy device without data preprocessing (top) and with exemplary data preprocessing (scattered light correction) (bottom).

Where: x: value in a column, $\bar{x}$: mean of the column, σ: standard deviation of the column values. The resulting matrix is then transposed back so that each row again contains a sample. Furthermore, in embodiments of the invention, for example, a multiplicative scattered light correction (MSC) can also be used for the scattered light correction in the NIR range. Both procedures are well-known standard procedures. FIG. 4 shows an exemplary NIR spectral overlay before and after data pretreatment.

Furthermore, it may be advantageous to differentiate NIR spectra (or other raw data matrices) before the actual analysis and/or to subject them to a smoothing algorithm. For these requirements, the Savitzky-Golay algorithm is used (see Citation [16]), which performs both data processing steps automatically.

If desired, a Principal Component Analysis (PCA) of the prepared raw data can be performed before the actual distance calculation. A subsequent distance calculation would then be based on the determined score values. This step can be useful when very noisy raw data needs to be processed. Before PCA, the data can also be centered, UV (univariance) or Pareto scaled (centering: $x'=x-\bar{x}$, UV scaling:

$$x' = \frac{x - \bar{x}}{\sigma},$$

Pareto scaling:

$$x' = \frac{x - \bar{x}}{\sqrt{\sigma}},$$

unlike stray light correction, no transposition of the data matrix before calculation). The user can then select the desired distance measure for the actual calculation. As a rule, this will be the Euclidean distance, but other distance measures are also conceivable, in particular the Manhattan distance, Pearson distance, Gower distance or the Mahalanobis distance.

After completing this pre-processing, the application now determines the start value or the "zero value" (in other words: the individual data points at time 0) for each sample contained in the meta data of the raw data, i.e. the chemical/physical/biological state of the sample, in particular—but not limited to—sugar content, disintegration rate, colour, breaking strength, disintegration time, friability, density, viscosity, refractive index and/or optical rotation angle before storage, e.g. under certain climatic conditions or targeted stress tests, such as irradiation with UV/VIS light, forcing redox reactions, or similar. The start value or zero value is defined or determined by the user. The metadata of the samples indicates exactly which samples or batches of samples were recorded at time 0. If there are several replicas of time 0 from a batch, the mean spectrum is calculated and stored in memory for later use. This so-called starting date of each corresponding sample then serves as a reference to which a distance calculation is carried out.

The distance is then calculated for each point in time, which can be determined from the metadata, for each batch or for each sample preparation according to the method selected by the user above. The distance values obtained in this way can then be sorted, aggregated and graphically displayed, as well as evaluated in more detail statistically.

In the described embodiment, an additional PCA is also calculated from the preprocessed raw data, which is not included in the distance calculation but supports a further, albeit purely qualitative, interpretation of the raw data.

Application Example 1—NIR Measurements of a Liquid Food: Orange Juice

The subject of the investigation was:

Orange juice "Beste Wahl" from REWE (100% juice from direct juice, with pulp, 8.5 g sugar per 100 ml (according to the label))

Opening the package and storing an aliquot at room temperature (22° C.)

Storage of another aliquot at 40° C., relative humidity=75%

A near-infrared spectroscopy device MPA II (Bruker Optik GmbH) was used as the measuring instrument:

Measurement of orange juice in transmission;

Wavenumber range: 12500 $cm^{-1}$ to 3950 $cm^{-1}$ (spectral ranges with an absorption>4.5 were not considered for the evaluation)

Data pretreatment of NIR spectra:

Formation of the 1st derivative with 9 smoothing points

The following calculation parameters were chosen:

Distance measure: Euclidean distance

Figure 5:
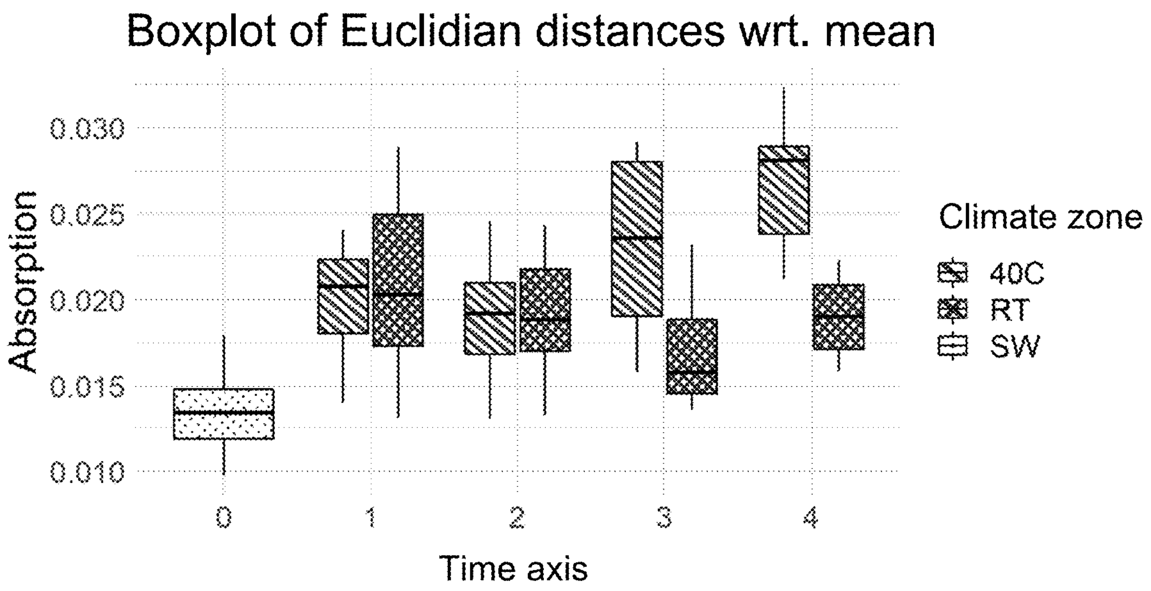
FIG. 5 shows the boxplot of a comparison of the determined Euclidean distances, calculated on the basis of NIR spectra of orange juice stored for several days at room temperature (="RT"), or 40° C. (="40° C.") ("SW"=starting value).

FIG. 5 shows the boxplot of the calculated distances over 5 days, where day 0 is the "starting value" (="SW"). In the first two days (day 1 and day 2) the change is practically identical under both storage conditions and there is no statistically significant difference. However, from day 3 onwards it becomes clear that the determined Euclidean distance of the samples at 40° C. increases significantly and also continues to increase on day 4 (Kruskal-Wallis test results in $p<0.05$, pairwise Wilcox test results in statistical significance on day 3 and day 4 with $p<0.05$, all other days not significant). This is consistent with the generally expected assumption that storage of food at elevated temperatures will lead to chemical or microbial changes (e.g. decomposition process of individual components or bacterial growth).

Application Example 2—NIR Measurements of a Solid Food: Minced Meat

The subject of the investigation was:

Freshly prepared minced pork from REWE

Storage of an aliquot immediately after purchase at room temperature (22° C.)

Storage of another aliquot at 40° C., relative humidity=75%

A near-infrared spectroscopy device MPA II (Bruker Optik GmbH) was used as the measuring instrument:

Measuring NIR spectra in diffuse reflection as absorption spectra

Wavenumber range: 12500 $cm^{-1}$ to 3950 $cm^{-1}$

Figure 6:
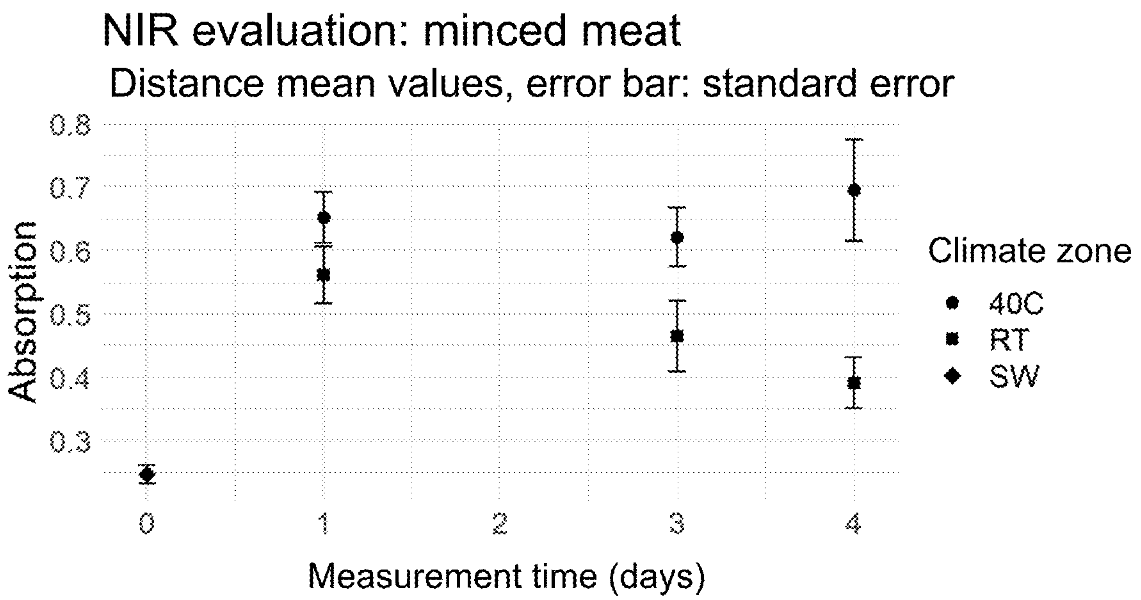
FIG. 6 shows the mean+/−standard error of the determined Euclidean distances, calculated on the basis of NIR spectra of minced meat samples stored for several days at room temperature (="RT"), or 40° C. (="40° C.") ("SW"=starting value).

Data pretreatment of the NIR spectra: performing an SNV scattered light correction The following calculation parameters were chosen: Euclidean distance FIG. 6 shows the mean values (error bars: standard errors) of the calculated Euclidean distances. In all cases, the biggest change occurs from day 0 to day 1. In general, it can be seen that, as expected, the minced meat changes more at higher temperatures than at room temperature (all time points differ statistically significantly with $p<0.05$ (Kruskal-Wallis or Wilcoxon rank sum test)) and the plateau formation in the 40° C. samples is not yet complete.

Figure 7:
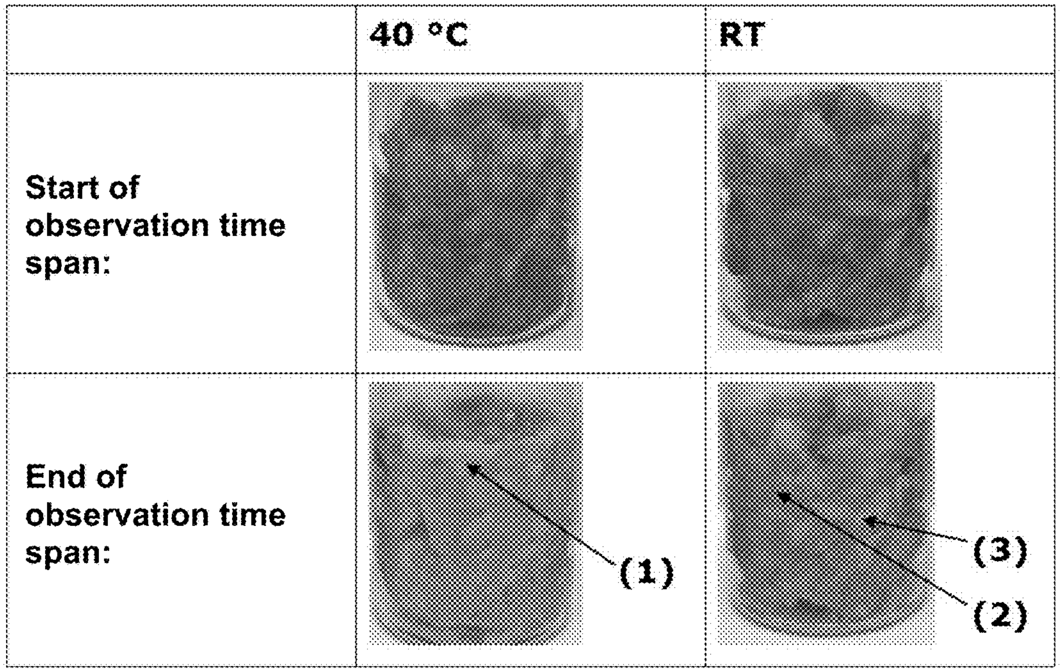
FIG. 7 shows the photographic change of the minced meat samples over the observed period at 40° C. and room temperature (RT). A clear change in the sample can be seen at 40° C. (1). At RT the marbling of the minced meat is clearly preserved (2 and 3). With the method according to the invention, however, this qualitative deterioration can be quantified and tracked much more precisely.

Parallel to the above measurements, a photo documentation (FIG. 7) was carried out (start and end of observation period). In the sample stored at elevated temperature, a clearly discolored "ring" (marked with (1)) is visible, and a liquid had formed on top of the meat sample that was not present in the room temperature sample. In addition, the texture of the sample (clear separation of meat portion (marked with (2)) & fat (marked with (3))) had changed significantly, which was much less pronounced in the comparison sample. These changes indicate that the food has spoiled.

Application Example 3—Online NIR Measurements of a Verbena Extraction

The subject of the investigation was:

150 g cut verbena (includes all dried above-ground plant parts)

Extraction in a beaker with stirring at 20° C. in 1800 ml demineralized water

A near-infrared spectroscopy device MPA II (Bruker Optik GmbH) was used as the measuring instrument. The samples to be measured were filtered before measurement.

Wavenumber range: 12500 $cm^{-1}$ to 3950 $cm^{-1}$ (spectral ranges with an absorption>4.5 were not considered for the evaluation)

Figure 8:
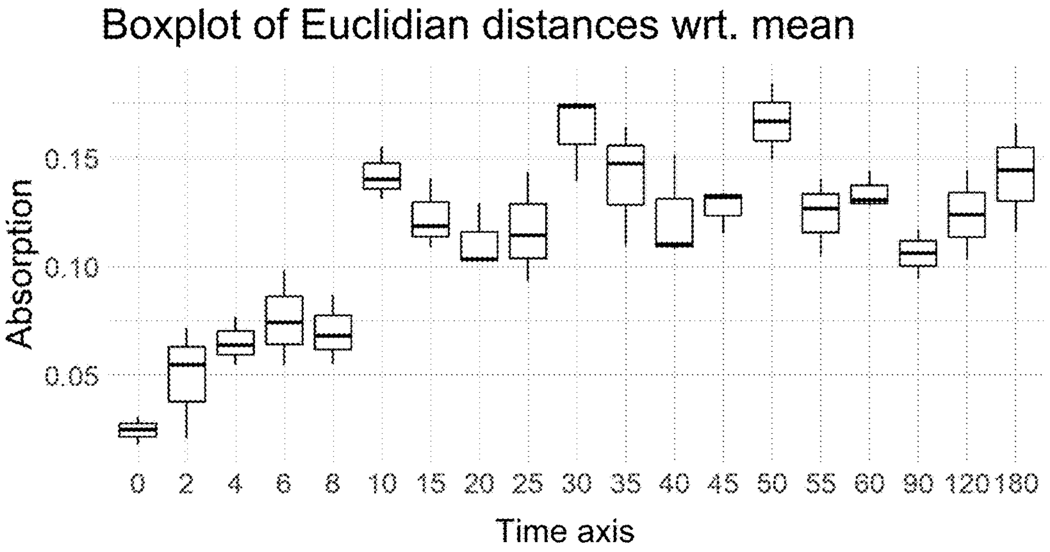
FIG. 8 shows the boxplot of a comparison of the determined Euclidean distances, calculated based on NIR spectra from an extraction experiment of verbena, which was carried out over a defined period of 180 minutes.

Data pretreatment of the NIR spectra: performing an SNV scattered light correction The following calculation parameters were chosen: Euclidean distance FIG. 8 shows the boxplot of the distances calculated with the new method over a period of 0 to 180 minutes of the extraction process. It is clear that the change in the solution as the extraction process progresses is larger at the beginning of the experiment and slowly reaches a plateau value towards the end. The decisive and new feature of the calculation method according to the invention, however, is that in this experiment not a single lead substance is tracked as a representative for the entire extraction process, but the entirety of the dissolved substances is tracked across the entire NIR spectrum. Different chemical plant constituents may exhibit different extraction rates/solubility kinetics. If only a single reference substance is used to assess an "exhaustive" extraction, it could be that this substance in its dissolution kinetics is not representative of all the substances contained. This could potentially result in an extraction being terminated prematurely because this lead substance no longer indicates any change in the solution after a certain period of time, even though other, undetected components have not yet completely passed into the solution. The present method eliminates this problem, since all substances in the solution are detected and thus a "total kinetics" of all dissolution processes can be recorded.

The recording of an identical extraction from production batch to production batch is particularly important in the production of pharmaceutical extracts, since the active ingredient content in the manufactured products must always be identical. Fluctuating active ingredient contents can lead to "out-of-specification" events in a subsequent quality control, the consequence of which may be the rejection of a production batch. The method according to the invention can help to significantly facilitate this requirement with little effort, or even make it possible in the first place.

Figure 9:
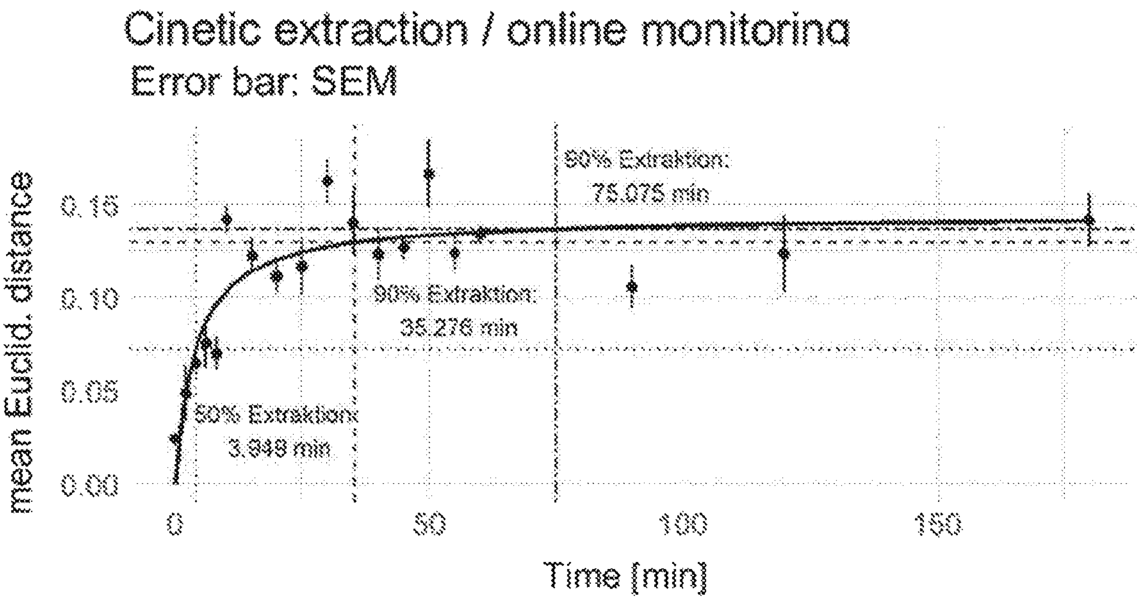
FIG. 9 shows a more detailed kinetic evaluation of the data from FIG. 8, in which in particular the rate constants ($Distanz_{max}$ and k) of the experiment were determined, as well as the estimated times required for a 50, 90 and 95 percent extraction.

FIG. 9 shows the overall kinetics calculated from the raw data of FIG. 8. Shown as points are the mean values with standard errors from the individual measurements of the box plot (from FIG. 8), as well as a subsequently calculated, non-linear kinetic curve. For this, the formula $$\text{Distance}(t) = \frac{\text{Distance}_{max} * t}{k + t}$$

was used. Another, adequate mathematical description could also have been used. Where Distance (t)=distance at time t; $\text{Distance}_{max}$=distance value in the plateau; k=speed constant.

From the kinetics presented in this example for the experiment carried out, it can also be deduced that the plant sample used after approx. 4 minutes to 50% extraction, a 90% extraction after approx. 35 minutes and a nearly exhaustive extraction of 95% is completed after about 75 minutes. This also means that the extraction can be terminated after 75 minutes and does not have to be continued unnecessarily for several more hours, which would entail considerable costs on an industrial scale.

Application Example 4—Tracking the Influence of Stress Factors on Cell Cultures Before the main experiment described below, a preliminary experiment was conducted to show whether HEK295 cells a) can grow confluently in NIR measuring vessels b) can be stressed by ethanol and, if so, in which concentrations, so that their viability/confluence decreases accordingly. This was verified in particular with the complex but proven trypan blue staining. For this purpose, concentrations of 0-10% ethanol were tested.

Based on the results of this preliminary test, it was decided to use two different concentrations of ethanol in the main test, since a clear influence on cell viability was seen in a period that could later be easily covered technically.

Subsequently, the main experiment was carried out, which confirmed the decrease in viability/confluence by an NIR measurement using the calculation method according to the invention.

The subject of the investigation was:

HEK295 cells, provided by Microbify, in a concentration of $2.2*10^5$ cells/ml in medium, grown confluently, i.e. adherently grown cells that have formed a continuous monolayer/cell layer, in the NIR measuring vessels with transflectance stamp made of stainless steel from BrukerOptics Use of nutrient medium DMEM (Dulbecco's Modified Eagle's Medium), with high glucose content, HEPES buffer, without phenol red indicator. Medium was purchased ready-to-use from ThermoFisher, catalog number 21063045, and mixed with 10% fetal calf serum (v/v) and 1% penicillin-streptomycin solution (v/v).

Cell culture for 48 hours before measurement directly in the measuring vessel

Addition of several concentrations of ethanol: 0% (control), 3%, 6% (each v/v). These EtOH concentrations were selected based on the preliminary experiment that induced a corresponding death/detachment response in a cell viability assay. Before the experiment began, the cells were confluent, i.e. 100% viable Measurement of cell changes via NIR over a period of 380 min The measuring instrument used was a near-infrared spectroscopy device microPHAZIR GP (Thermo Fisher Scientific Inc.) with a wave number range: 6266 $cm^{-1}$ to 4172 $cm^{-1}$ Data pretreatment of the NIR spectra: No special pretreatment was carried out, spectra were processed directly.

The following calculation parameters were chosen: Euclidean distance

The cells were removed from the incubator and treated with a chemical stress factor (ethanol) at the concentrations mentioned. Three independent replicates were prepared with 0%, 3% and 6% ethanol and in a narrow measured at intervals of time (every 2 minutes) over a total period of 6 hours via NIR.

Figure 10:
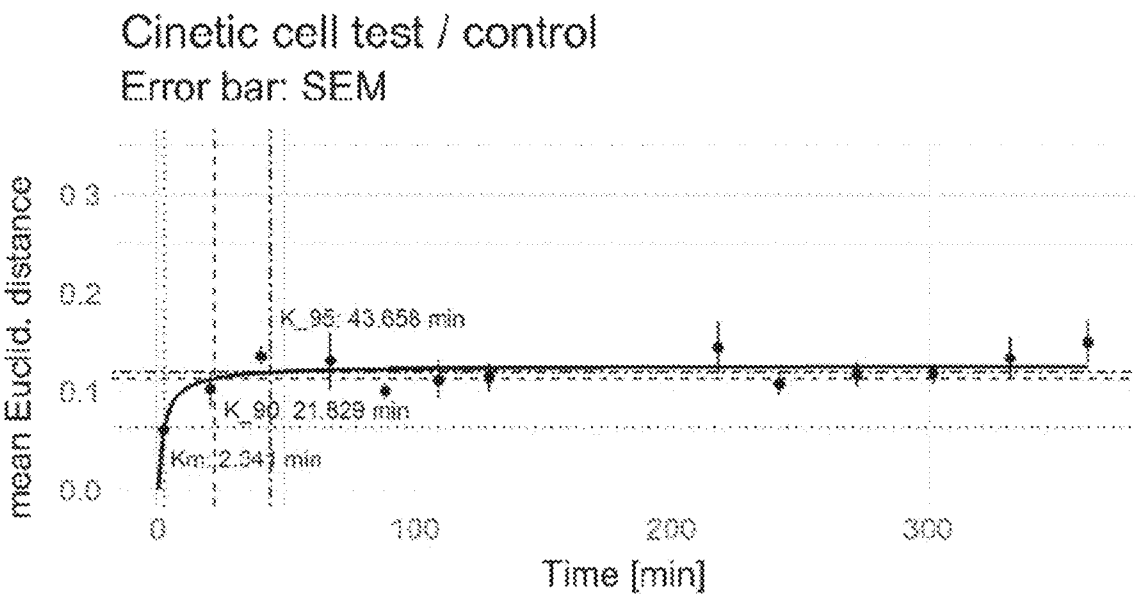
FIG. 10 shows a more detailed kinetic evaluation of data from a cell culture experiment, here an untreated HEK295 cell culture without additional stress agent (=control). The times until reaching 50% ($K_m$), 90% and 95% of a plateau value were determined.
Figure 11:
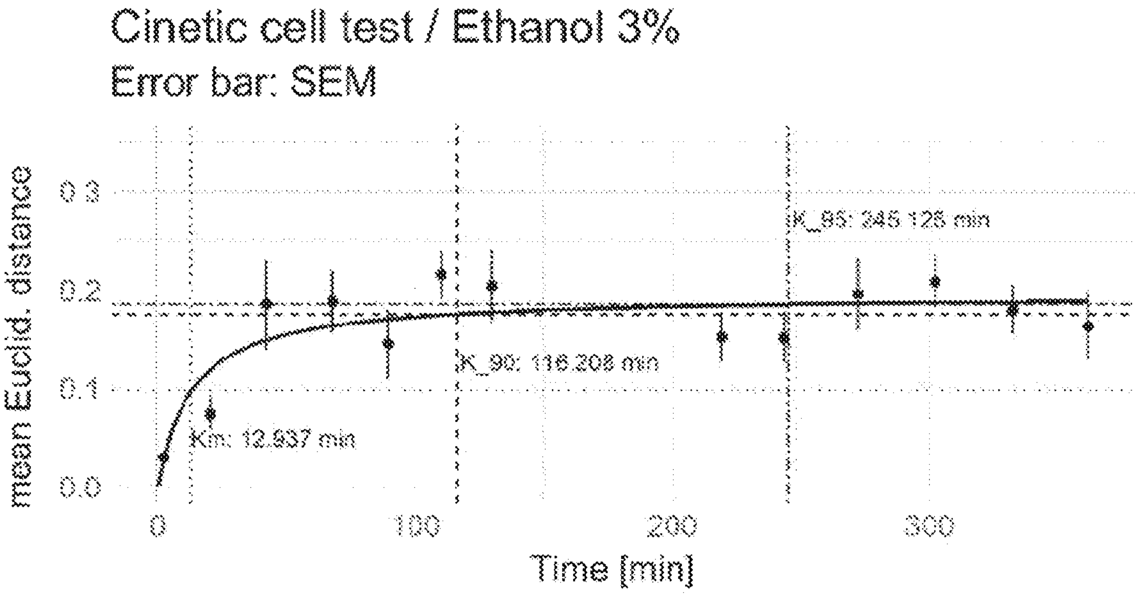
FIG. 11 shows the detailed kinetic evaluation of data from a cell culture experiment under the influence of a 3% ethanol solution, which was added as a stress agent. The times until reaching 50% ($K_m$), 90% and 95% of a plateau value were determined. The different viabilities and kinetics (see also FIG. 12) can be correlated very well with the preliminary experiment (Example 4), in which considerably more concentrations were tested.
Figure 12:
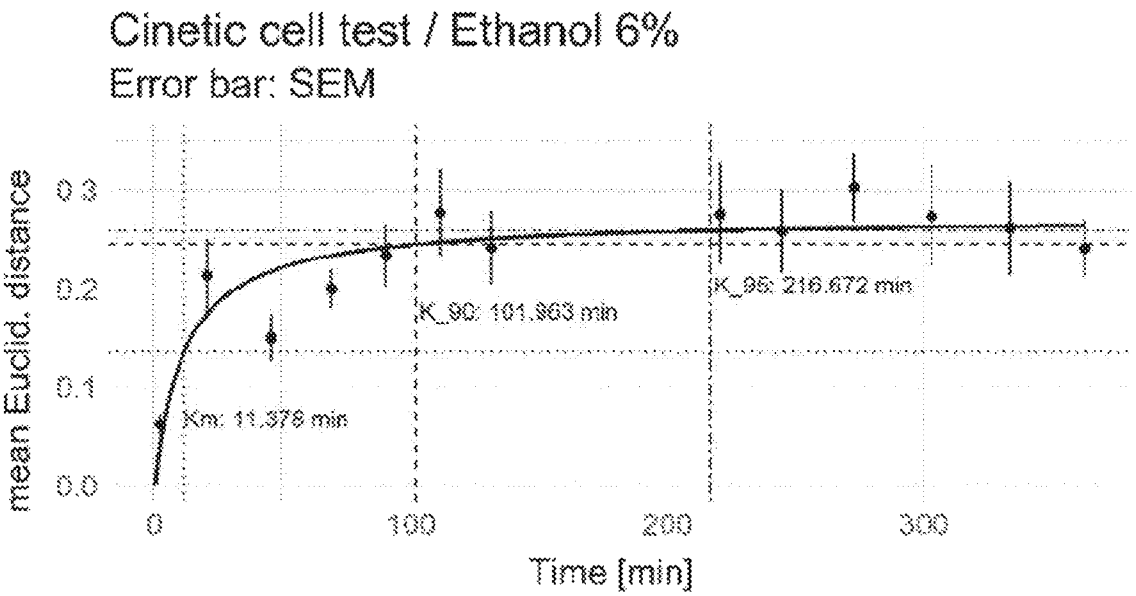
FIG. 12 shows the detailed kinetic evaluation of data from a cell culture experiment under the influence of a 6% ethanol solution, which was added as a stress agent. The times until reaching 50% ($K_m$), 90% and 95% of a plateau value were determined.

From the measured spectra, the Euclidean distances were calculated according to the method of the invention, averaged per measurement time and the fitting of kinetic curves (cf. Application example 3; identical procedure). These are shown in FIGS. 10, 11 and 12, for control, treatment with 3% ethanol and 6% ethanol, respectively. The data points are the mean values of 3 independent replicates, each measured 3 times, thus there are 9 measurement points per point. The error bars are the standard error of the mean. Also shown are the determination points for $K_m$ (time at which 50% of the plateau value was reached), $K_{90}$ (time at which 90% of the plateau value was reached), and $K_{95}$ (time at which 95% of the plateau value was reached).

These values are reached very quickly in the control ($K_m$~2.4 min, $K_{95}$~43.7 min), whereby the plateau value itself also takes the lowest value within the experiments.

Apparently, removing the cells from the incubator and using them on the laboratory bench is already a minor stress factor. The $K_m$ values of the ethanol-stressed cells are statistically identical (at 3% EtOH~13 min, at 6% EtOH~11 min), which could be due to a uniform, concentration-independent initial reaction of the cells to the addition of ethanol.

Figure 13:
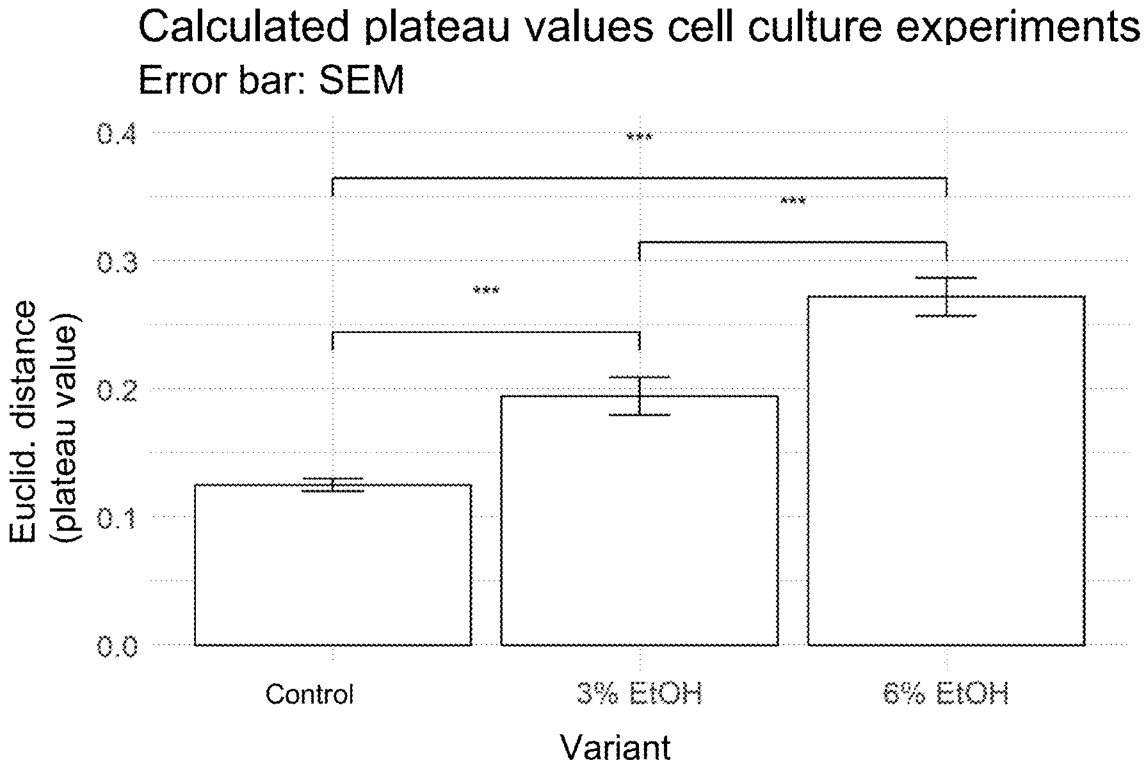
FIG. 13 shows the summary of the determined plateau values from the cell culture experiment. The distance value determined for the approach with 6% ethanol is the largest, which suggests a strong influence of this high concentration on the cell culture. This measurement approach is therefore the most "unstable". The value for the 3% and control approach is correspondingly lower. These results are also reflected by the previously performed cell viability assay.

However, when ethanol is added in different concentrations, a higher plateau is gradually reached, which indicates a significantly higher stress load on the cells. This is also consistent with the fact that the cells in the measuring vessels (as already observed in the preliminary experiment) detached from the surface over time and lost their confluence. This is also clearly evident from the bar chart (FIG. 13) (statistical significance, one-way ANOVA with $p<0.001$; post-hoc test: pairwise t-test, all p-values $<0.001$), which was generated from the parameters of the curve fits from FIGS. 10, 11 and 12.

Here, too, the crucial innovation is that in order to detect cell stress, a representative individual substance does not have to be identified, isolated and quantified from the cell suspension, nor does it require the establishment and implementation of complex cell staining and counting assays, which, moreover, cannot be designed as online measurements, for example. Instead, a very high sample volume can be directly measured spectroscopically without complex external sample preparation and evaluated with little effort using the method according to the invention. In addition, it was demonstrated here that the present method can also be successfully used to monitor the stability/viability of living cells.

Figure 14:
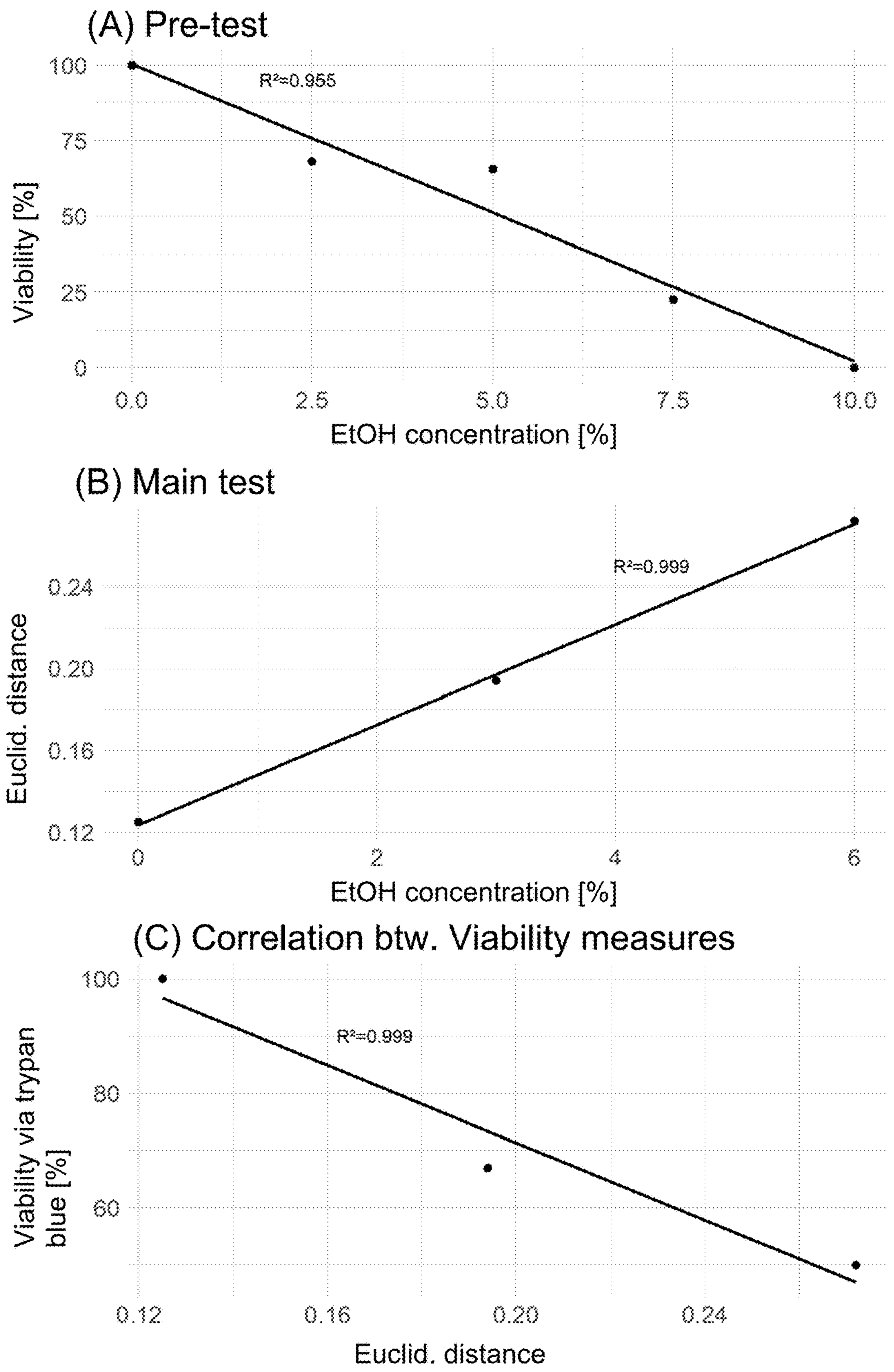
FIG. 14 shows the correlation between cell viability and used ethanol concentration (in %) in the preliminary experiment (A), observed maximum Euclidean distance and used ethanol concentration (in %) in the main experiment (B), as well as the correlation of cell viability and observed maximum Euclidean distance (C), which relates both analytical techniques. For each subgraph (A), (B) and (C) a linear trend line was added, each with an $R^2$ of 0.955, 0.999, and 0.999, respectively.

The observed cell viability at the end of the preliminary experiment (which was linearly interpolated due to slightly different EtOH concentrations used) correlates with the observed maximum Euclidean distances (with $R^2$>95%) (see FIG. 14, and the table shown below).

TABLE 2

Comparison of distance measures calculated as Euclidean distance with the results of a colorimetric cell viability assay (staining with trypan blue).

| | Pre-test: cell viability | Main test: maximum Euclidian distance |
|---|---|---|
| 0% ethanol | 100% | 0.125 |
| 2.5% ethanol | 68% | (not measured) |
| 3% ethanol | 70.84% (interpolated) | 0.194 |
| 5% ethanol | 65.5% | (not measured) |
| 6% ethanol | 41.38% (interpolated) | 0.272 |
| 7.5% ethanol | 22.5% | (not measured) |
| 10% ethanol | 0% | (not measured) |

Application Example 5—Comparison of a Medicinal Product (Medicinal Tea) with a Photometric Reference Method The subject of the investigation was:

Medicinal tea: Bad Heilbrunner liver and gall tea (1 filter bag with 1.75 g contains according to the manufacturer: 0.61 g peppermint leaves, 0.35 g dandelion, 0.26 g, Javanese turmeric, 0.18 yarrow herb; no quantity specified: fennel, chamomile flowers, caraway, liquorice root)

Extraction of 3 tea bags in a beaker under reflux (boiling temperature of water, approx. 100° C.) in 150 ml demineralized water A near-infrared spectroscopy device MPA II (Bruker Optik GmbH) was used as the measuring instrument. The samples to be measured were filtered before measurement.

Wavenumber range: 12500 $cm^{-1}$ to 3950 $cm^{-1}$ spectral ranges with an absorption>4.5 were not considered for the evaluation)

Data pretreatment of the NIR spectra: performing an SNV scattered light correction The following calculation parameters were chosen: Euclidean distance A validated photometric method for the detection of total polyphenols (measurement of the absorption at 760 nm after reacting the solution with a molybdate-tungstate reagent and 29% sodium carbonate solution, based on Monograph 2.8.14 of the European Pharmacopoeia) was used as a reference method.

The aim of the study was to determine whether a spectroscopic analysis of the tea samples at time 0 and 10 days when the sample was stored at 4° C. in the refrigerator (KS), at 20° C. (room temperature, RT) and at 40° C. could demonstrate a similar recovery rate/stability as a validated, photometric reference method that detects total polyphenols (GPP) in a solution.

Figure 15:
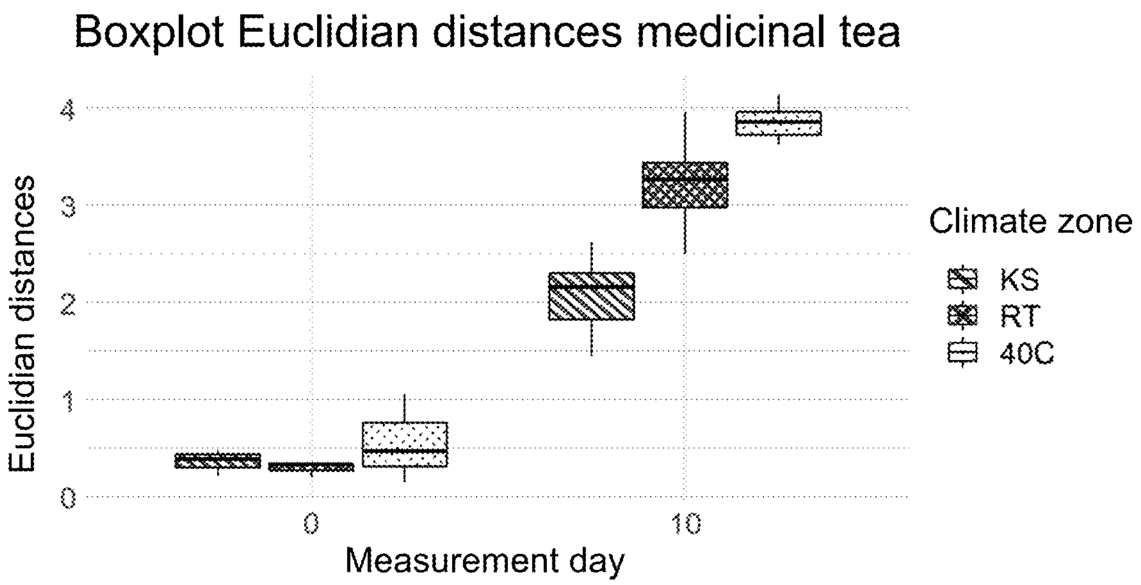
FIG. 15 Boxplot of the Euclidean distances of a NIR measurement of a medicinal tea preparation under different storage conditions (refrigerator (RF)/room temperature (RT)/40° C. climate chamber).

FIG. 15 shows the determined Euclidean distances from the NIR measurements on day 0 and day 10. These increase the least in samples stored in the refrigerator (KS), moderately when stored at room temperature (RT) and most strongly at 40° C., which is intuitively expected.

Figure 16:
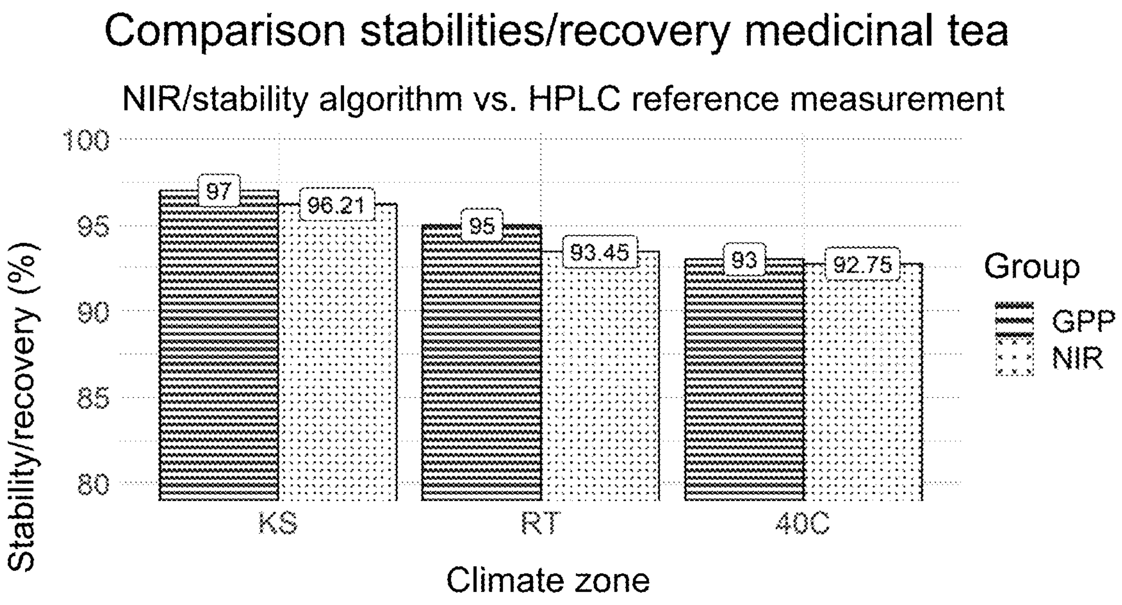
FIG. 16 Comparison of stability measurements of a medicinal tea preparation. Measurements were taken using a validated reference method (photometric assay in the UV/VIS range, referred to as GPP in the legend), as well as using NIR using the new evaluation method according to the invention.
Figure 17:
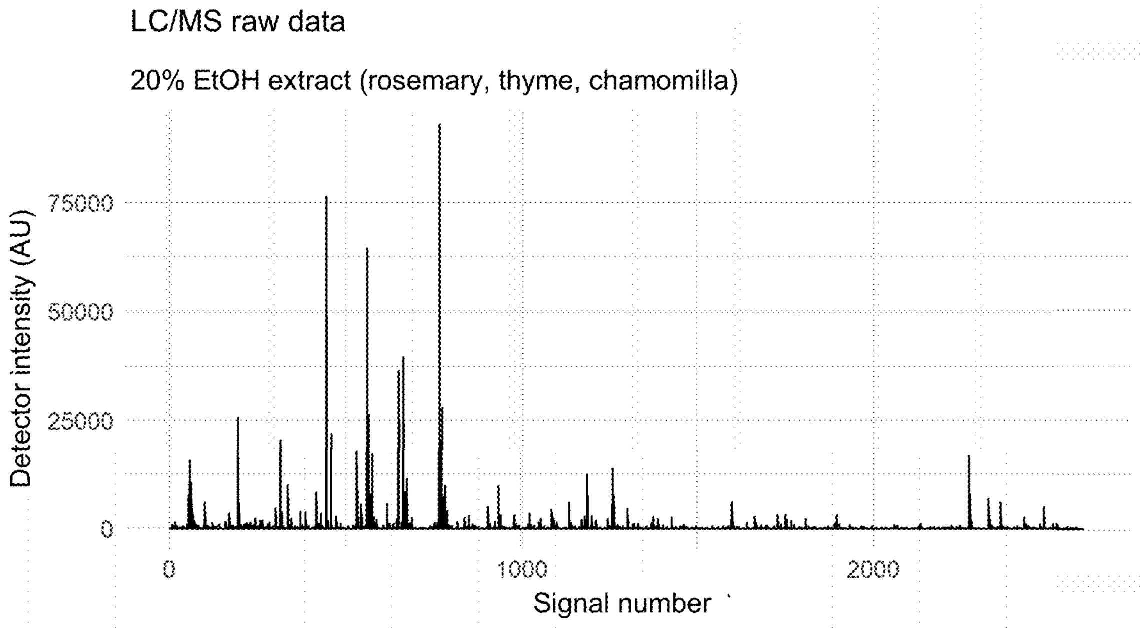
FIG. 17 Exemplary graphical representation of the HPLC/MS raw data set for the 20% ethanolic extract of a medicinal drug mixture of thyme, rosemary and chamomile. This raw data was processed directly using the new evaluation method.

The comparison with the recovery rates or stability from the photometric method (labeled "GPP" in legend) in FIG. 16 also shows that the new calculation using distance measures is in good agreement with this reference. The fact that it is somewhat lower than in the reference method is understandable, since the new method detects all substances in the mixture, whereas the reference method only detects a subset.

To calculate a percentage stability rate, a hypothetical blank spectrum without analytes was assumed for the NIR data and its Euclidean Distance to the averaged output spectrum is calculated. This distance was then used to normalize all other distances in this interval. For the reference method, the total polyphenols were determined in mg/100 g and their degradation after 10 days was also standardized to a percentage value.

Figure 18:
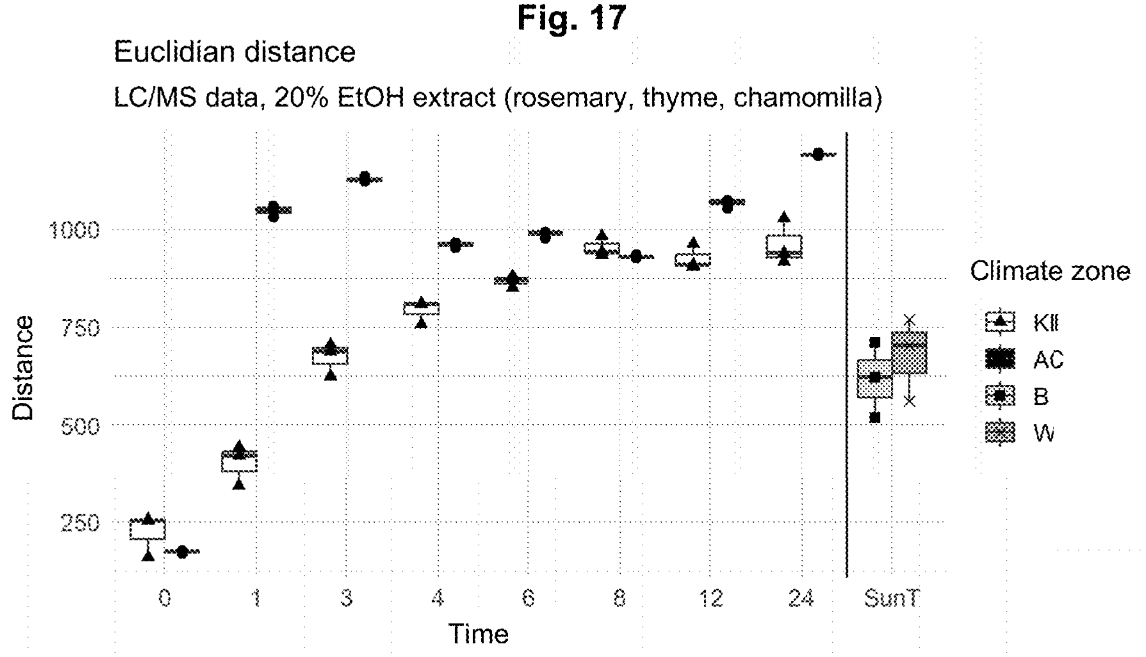
FIG. 18 Boxplot representation of the calculated Euclidean distances to the HPLC/MS data set for the 20% ethanolic extract shown in FIG. 17. The Euclidean distances were plotted against the weekly values (observation period 24 weeks) or on the far right after irradiation with light (SunT). Explanation Legend: KII=climate zone II; AC=climate zone AC; B=amber glass bottle; W=white glass bottle.

Application Example 6—Comparison of an Extract Mixture in Different Climate Zones Using HPLC/MS The objects of the study were:

Ethanolic-aqueous extract of a medicinal plant mixture of thyme, rosemary and chamomile (1:1:1) using a 20% ethanolic-aqueous mixture Storage conditions:

AC (Accelerated conditions): Temperature=40° C., relative humidity=75% KII (climate zone II): Temperature=25° C., relative humidity=60% Storage for 24 weeks in each case An additional, independent sample: Irradiation for 20 hours at 150 klx in the Sun Tester in amber glass/white glass vials (labeled "B" or "W" in the figure legend of FIG. 18)

Device used: Suntest CPS+ (Atlas Material Testing Technology GmbH)

Wavelength: 320 nm to 800 nm

Irradiation dose: 3000 klx*h

The following devices were used as measuring instruments:

Chromatographic system: 1290 Infinity II (Agilent Technologies Germany GmbH & Co. KG)

Detector: TripleTOF (Sciex)

The following calculation parameters were selected:

Distance measure: Euclidean distances

Calculation on LC/MS peaktable (2602 single signals)

Pre-processing: Calculation on latent variables, variance coverage >95%

For the kinetics calculations (FIG. 19), the equation $$\text{Distance} = \frac{\text{Distance}_{max} * t}{k + t}$$

was used and $\text{Distance}_{max}$ and k were determined mathematically.

Figure 19:
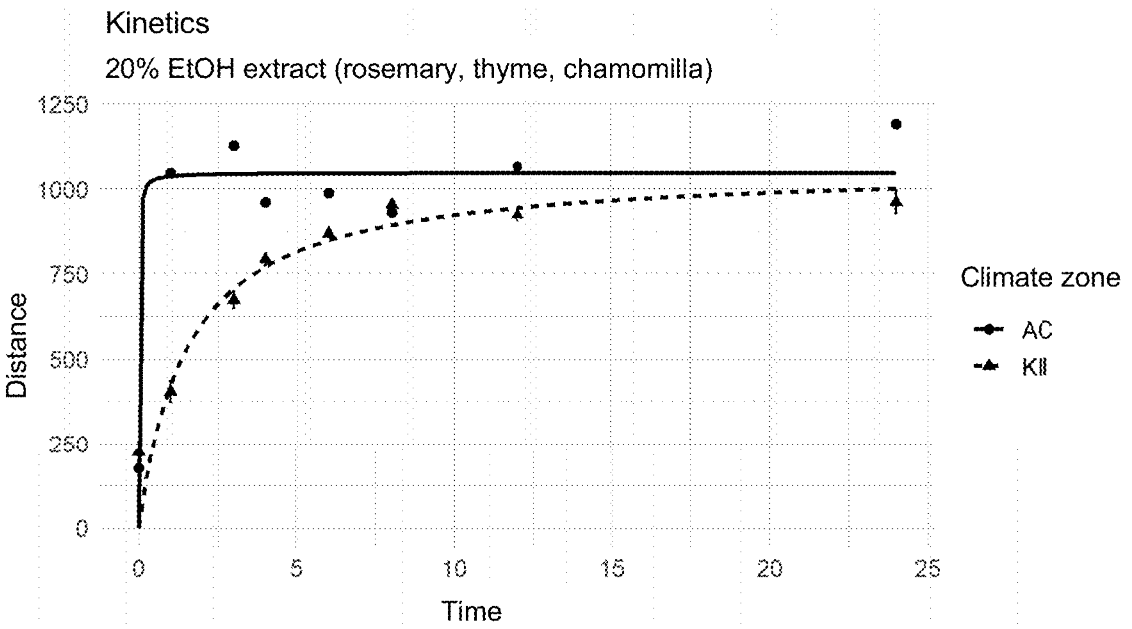
FIG. 19 Fit of the determined kinetic function for the Euclidean distances calculated from the HPLC/MS raw data for the 20% ethanolic extract of FIG. 17. Explanation Legend: KII=climate zone II; AC=climate zone AC.

The results of the investigation are shown in FIG. 19. It can be clearly seen that the changes occur much faster in the stricter climate condition ("AC"), as a higher distance is reached earlier, although the samples in both climate conditions reach practically the same distance plateau towards the end of the test.

By irradiating the samples in the Suntester (see FIG. 18), the same level of change is reached within approx. 20 hours that would otherwise only be achieved after approx. 3.5 weeks of storage under climate zone II conditions, with no significant difference between amber and white glass vials.

Figure 20:
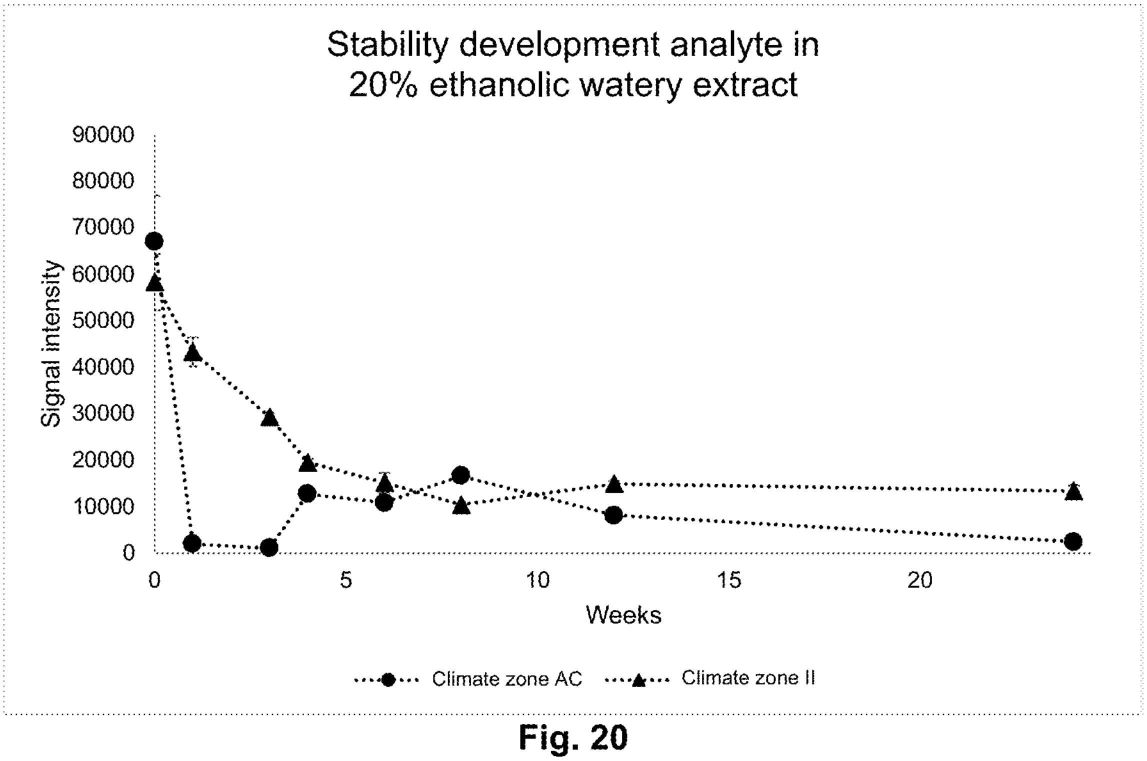
FIG. 20 Stability curve of the 20% extract of a medicinal drug mixture of thyme, rosemary and chamomilla over a representative, single, selected marker compound (m/z 329.17; retention time=8.16 min) under different climatic conditions.

A classical approach using a representative marker substance (m/z 329.17; retention time=8.16 min, FIG. 20) shows, as in the NIR evaluation, an expected degradation of the compound over time, which reaches the end point significantly faster in condition AC than in condition climate zone II. In contrast to the processing of a data set containing the information of many compounds (as here NIR spectra), this analytical approach with only a single marker substance shows only a very limited picture of this product and cannot really represent the entire multi-compound mixture.

In addition, the evaluation of data sets relating to individual compounds is significantly more complex and time-consuming.

Application Example 7—Comparison of Packaging Materials Using NIR Under the Influence of Irradiation with Intense Light and Elevated Temperature The subjects of the study were:

A medicinal drug powder mixture of rosemary, thyme and chamomile in a ratio of 1:1:1

Storage conditions: closed in a paper bag (="P1") or stored open (="P2")

Irradiation with light was carried out under the following conditions:

Device: Suntest CPS+ (Atlas Material Testing Technology GmbH)

Wavelength: 320 nm to 800 nm

Irradiation dose: 3000 klx*h

A near-infrared spectroscopy device MPA II (Bruker Optik GmbH) was used as the measuring instrument:

Measurement in diffuse reflection

The following calculation parameters were selected:

Distance measure: Euclidean distance

Calculation on SNV-corrected NIR spectra without any restriction of wavenumber ranges Distance calculation on latent variables with covered total variance>95%

Figure 21:
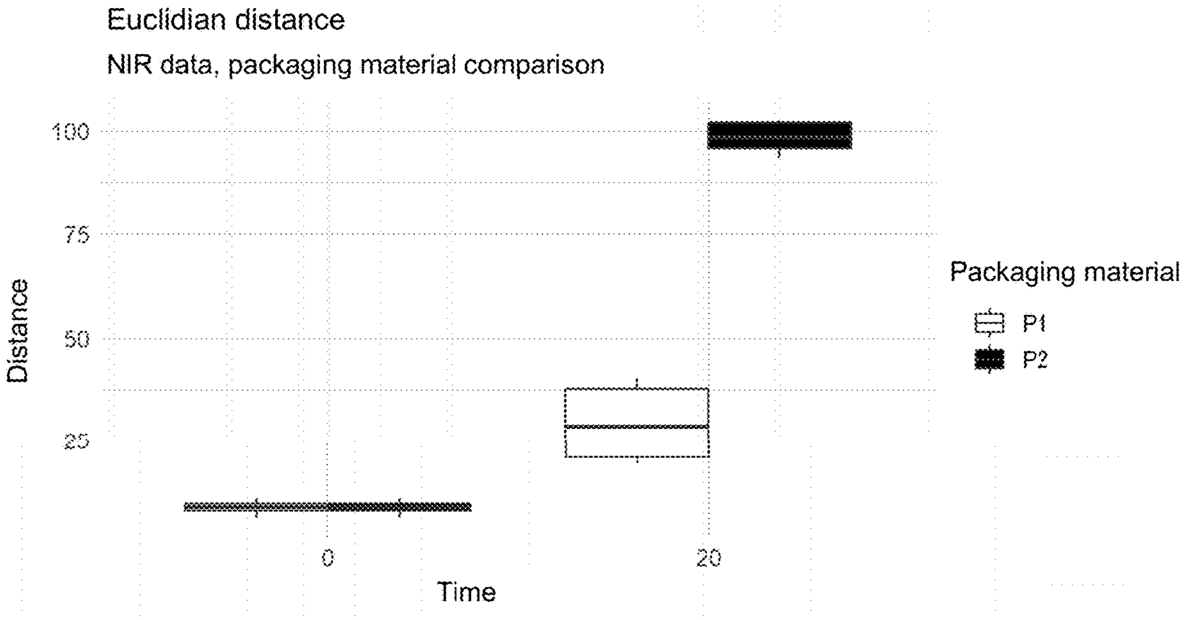
FIG. 21 Boxplot representation of the Euclidean distances of a medicinal drug powder mixture of rosemary, thyme and chamomile before (time 0) and after irradiation with light for 20 hours (time 20). Explanation Legend: P1=powder mixture packed in paper bag; P2=powder mixture stored open.
Figure 22:
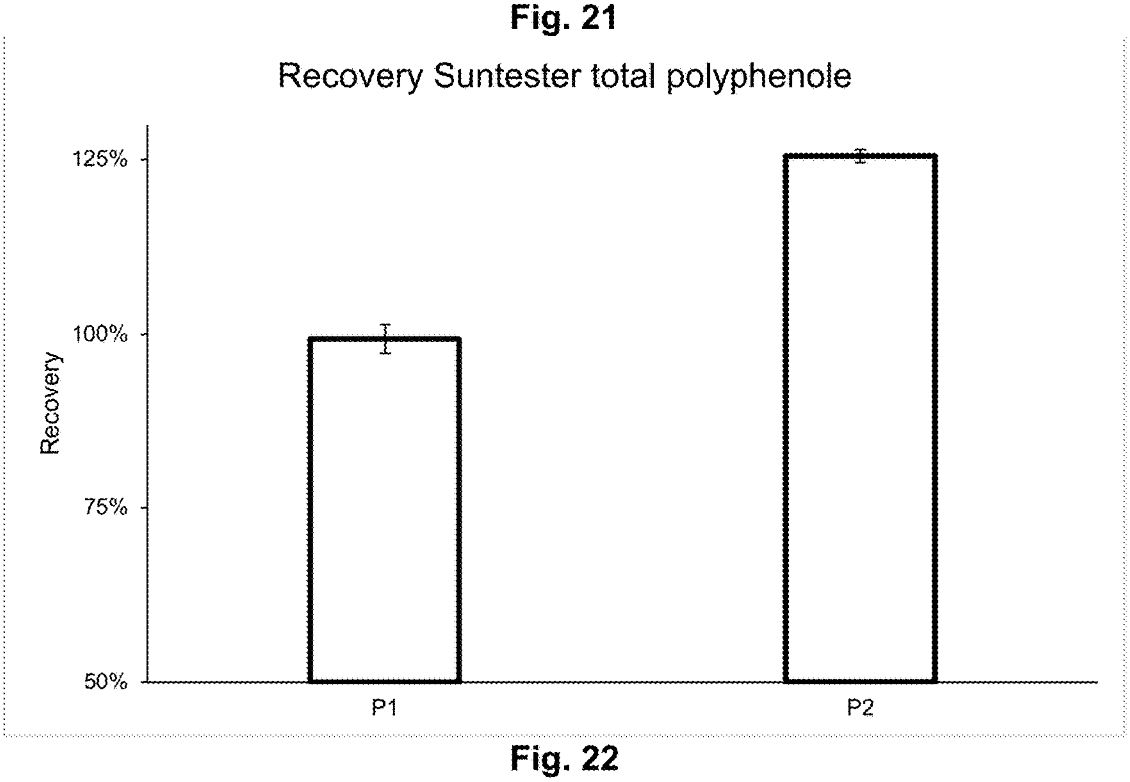
FIG. 22 Column diagram for the reference data using wet-chemical photometric determination of total polyphenols based on monograph 2.8.14 of the European Pharmacopoeia. A drug powder mixture was irradiated with light for 20 hours, on the one hand packed in a paper bag (P1) and on the other hand stored open (P2). The recovery is to be interpreted as the percentage agreement between the absorbance after irradiation and the initial value of the unstressed sample.

The following was recorded as the result of the investigation:

The result is shown in FIG. 21 in the form of a boxplot. At time 0 (before starting the irradiation in the Sun Tester) the distance values in both samples are identical, but the values at time 20 hours are not only different from the starting value, but also P1 (powder mixture in paper bag) and P2 (openly stored powder mixture) are significantly different from each other. This is partly due to the strong exposure to light (hence the sharp increase in sample P2), but also to the increased temperature reached here in the Sun Tester, which also affects sample P1 (in the paper bag). These results were also confirmed by a classic analysis method. The total polyphenols were determined photometrically in accordance with the general monograph 2.8.14 of the European Pharmacopoeia, which is a very complex wet-chemical analysis method. Here too, sample P2 showed a clear deviation from the initial value (difference from initial value=26%), whereas sample P1 (difference from initial value=1%) remained almost unchanged in the paper bag (see FIG. 22).

The method according to the invention thus makes it impressively clear that temperature and light exposure together have a measurable influence compared to only thermal exposure or no exposure to the two factors. The very time-consuming wet chemical analysis of the polyphenols confirms the occurrence of changes in the sample, but can only show a part of these changes, since polyphenols only represent a section of the entire chemical profile. In contrast, the method according to the invention captures the complete profile and therefore shows a much more comprehensive picture.

Application Example 8—Comparison of Different Climate Zones Using NIR

The objects of the investigation were:

A powdered medicinal drug mixture of rosemary, thyme and chamomile in a ratio of 1:1:1

Storage Conditions:

AC (Accelerated conditions): Temperature=40° C., relative humidity=75%

KII (climate zone II): Temperature=25° C., relative humidity=60%

Storage for 24 weeks in each case

A near-infrared spectroscopy device MPA II (Bruker Optik GmbH) was used as the measuring instrument:

Measurement in diffuse reflection

The following calculation parameters were selected:

Distance measure: Euclidean distance

Calculation on SNV-corrected NIR spectra without any restriction of wavenumber ranges Distance calculation on latent variables with covered total variance>95%

The following devices were used as measuring instruments for the parallel, classical analytical approach:

Chromatographic system: 1290 Infinity II (Agilent Technologies Germany GmbH & Co. KG)

Detector: TripleTOF (Sciex)

Figure 23:
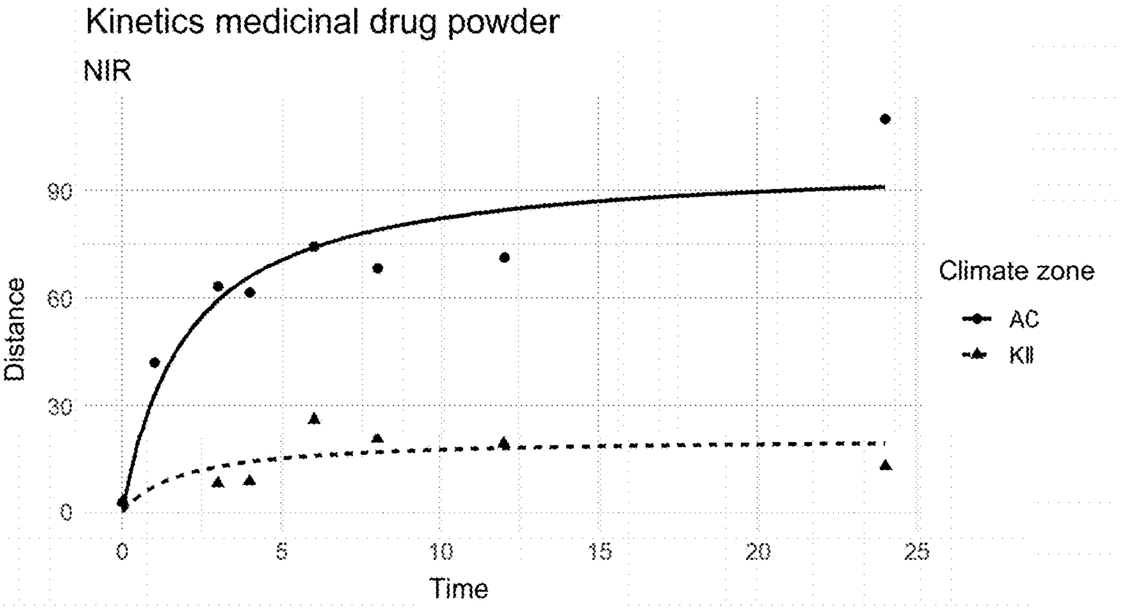
FIG. 23 Fit of the determined kinetic function for the Euclidean distances calculated on latent variables on the basis of the NIR spectra (SNV-corrected) for a drug powder mixture over an observation period of 24 weeks in different climatic zones. Explanation Legend: KII=climate zone II; AC=climate zone AC.
Figure 24:
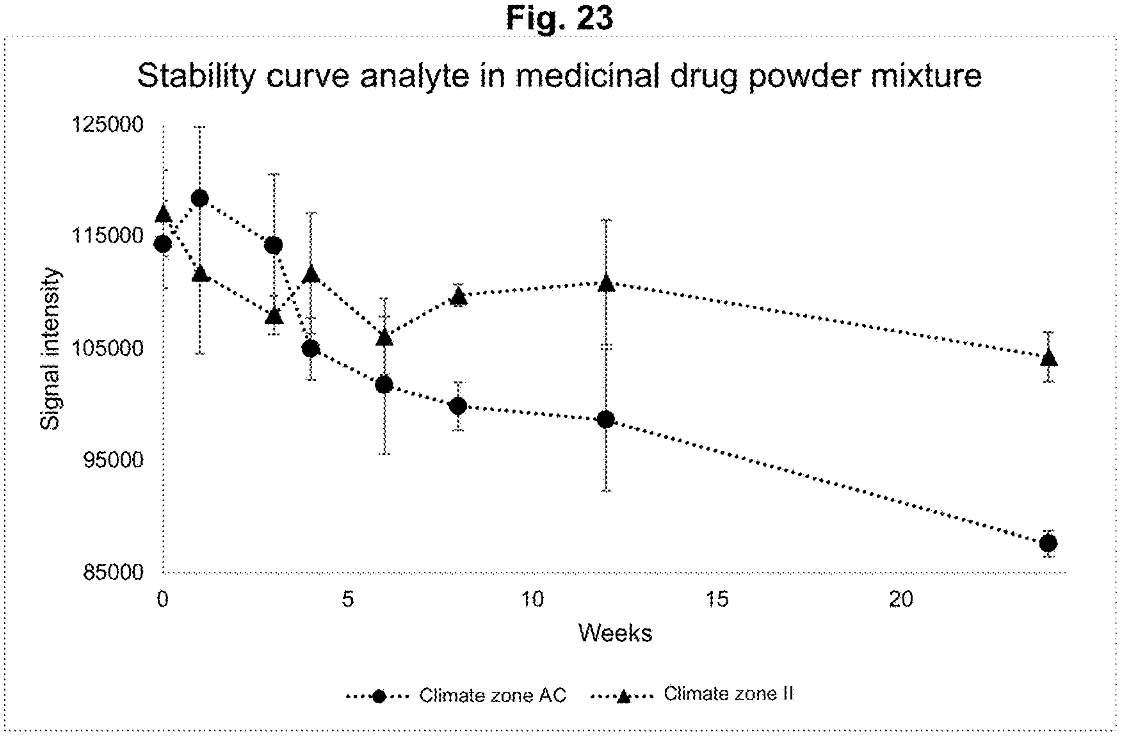
FIG. 24 Stability curve of a drug powder mixture over a representative, single, selected marker compound (m/z 329.17; retention time=8.16 min) under different climatic conditions.

The following was recorded as a result of the investigation:

FIG. 23 immediately shows that the stricter climate zone AC already lead to significantly higher distances in the first week compared to climate zone II. This of course corresponds to expectations, which is also mapped in parallel using a classical analytical approach via HPLC/MS using a single representative compound. FIG. 24 shows the course of the signal intensity of a main compound (m/z=329.17; retention time=8.16 min) from the powder mixture. Here, a significantly faster degradation can be seen in climate AC than in climate zone II, but this classic approach with consideration of only a single substance does not do justice to the complexity of a plant product; the new approach considers a large data set for a complex product in its entirety. Analogous to example 1, kinetics were also calculated here for the two different climate zones over the distances determined from the NIR data set.

Figure 25:
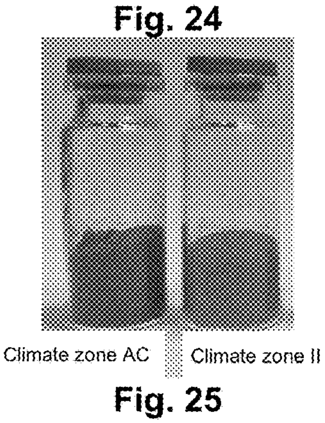
FIG. 25 Optical change of a drug powder mixture after storage in different climatic zones after 24 weeks. The sample of the mixture stored in climate zone AC is clearly darker in color.

The change after 24 weeks is also visually apparent (FIG. 25), in which the powder in the sample vial of climate zone AC is significantly darker in color than its counterpart in climate zone II, but this purely visual assessment is very subjective and generally difficult to record. Our calculation method, on the other hand, makes this change not only qualitatively but also quantitatively detectable.

Application Example 9—Comparison of Packaging Materials of A Solid Pharmaceutical Form Using NIR The objects of the study were:

Hawthorn film-coated tablets:

Each film-coated tablet contains 450 mg dry extract of hawthorn leaves with flowers The film-coated tablets were stored firstly in a blister in a folding box and secondly filled in polyethylene bags Storage Conditions:

AC (Accelerated conditions): Temperature=40° C., relative humidity=75%

KII (climate zone II): Temperature=25° C., relative humidity=60%

Storage for 24 weeks in each case

A near-infrared spectroscopy device MPA II (Bruker Optik GmbH) was used as the measuring instrument:

Measurement in diffuse reflection

The following calculation parameters were selected:

Distance measure: Euclidean distance

Calculation on SNV-corrected NIR spectra without any restriction of wavenumber ranges The following devices were used as measuring instruments for the parallel, classical, analytical approach:

Chromatographic system: 1290 Infinity II (Agilent Technologies Germany GmbH & Co. KG)

Detector: TripleTOF (Sciex)

Figure 26:
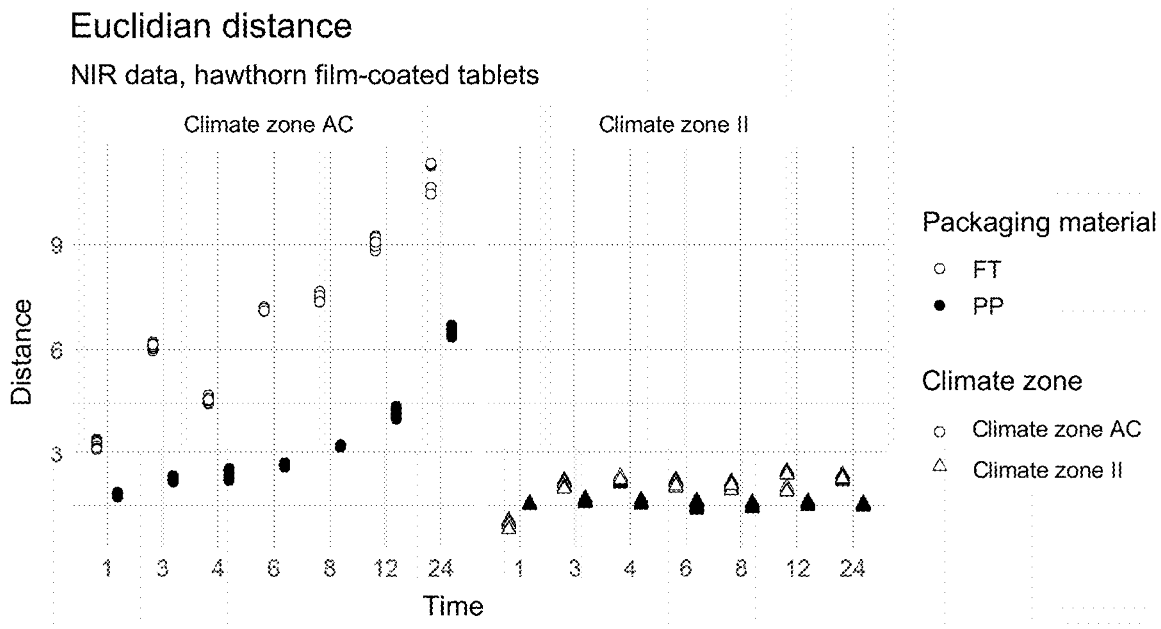
FIG. 26 Boxplot representation of the calculated Euclidean distances from an NIR data set (SNV-corrected) of hawthorn film-coated tablets. The Euclidean distances were plotted against the weekly values (observation period 24 weeks). Explanation Legend: FT=film-coated tablets in polyethylene bag; PP=film-coated tablets in blister and folding box.
Figure 27:
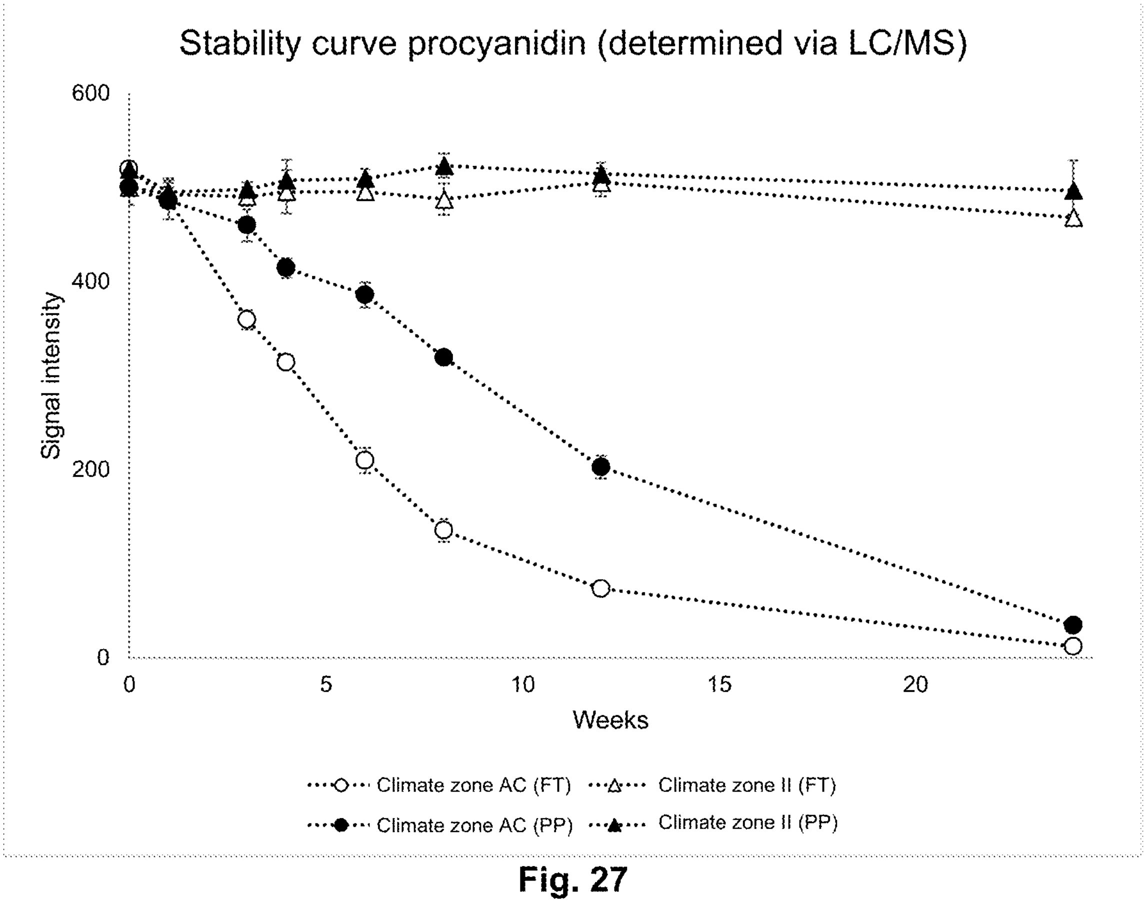
FIG. 27 Stability curve of hawthorn film-coated tablets via a representative dimeric procyanidin (m/z 577.14; retention time=2.69 min) under different climatic conditions and different packaging materials. Explanation Legend: FT=film-coated tablets in polyethylene bag; PP=film-coated tablets in blister and folding box.

The evaluation of the NIR data set shows an expected result. On the one hand, the distance increases significantly faster under AC climatic conditions and also reaches higher maximum values over a period of 24 weeks; on the other hand, a stabilizing effect of the higher-quality packaging material in the form of blisters in combination with a folding box (labelled "PP" in the figure legend) in contrast to the polyethylene bags (labelled "FT" in the figure legend) can be clearly derived (see FIG. 26). The same result can also be derived using a representative marker compound (dimeric procyanidin, m/z 577.14; retention time=2.69 min) in a classic evaluation approach (see FIG. 27). Here, too, the samples from climate zone II show an extensive constancy and climate zone AC a clear, rapid degradation; however, the classic approach is associated with a significantly higher measurement and evaluation effort and is not able to represent the corresponding product in its full material complexity; the novel method solves both limitations, since no specific selection and processing of individual raw data points by a user is required, but the complete overall spectrum of substances is recorded via the NIR spectra and the new method is guaranteed to reflect the behavior of the sample under investigation.

It is understood that aspects of the embodiments described here which have been described in the context of a device also represent a description of a corresponding method. Some or all of the method steps may be performed by (or using) a hardware device, such as a processor, a microprocessor, a programmable computer, or an electronic circuit. In some embodiments, one or more of the key method steps may be performed by such a device.

Embodiments of the invention may be implemented in hardware and/or software. The implementation can be carried out with a non-volatile storage medium such as a digital storage medium such as a floppy disk, a DVD, a Blu-Ray, a CD, a ROM, a PROM and EPROM, an EEPROM or a FLASH memory on which electronically readable control signals are stored which (can) interact with a programmable computer system so that the respective method is carried out. Therefore, the digital storage medium can be computer-readable. Some embodiments according to the invention comprise a data carrier with electronically readable control signals that can interact with a programmable computer system so that one of the methods described herein is carried out.

In general, embodiments of the present invention may be implemented as a computer program product having a program code, wherein the program code is effective for carrying out one of the methods when the computer program product is running on a computer. The program code can, for example, be stored on a machine-readable medium. Further embodiments include the computer program for carrying out one of the methods described herein, which is stored on a machine-readable carrier.

Another embodiment of the present invention is a storage medium (or a data carrier or a computer-readable medium) having a Computer program for carrying out any of the methods described herein when executed by a processor. The data carrier, the digital storage medium or the recorded medium is usually tangible and/or not seamless. Another embodiment of the present invention is an apparatus as described herein comprising a processor and the storage medium.

Another embodiment of the invention is a data stream or a signal sequence representing the computer program for carrying out one of the methods described herein. For example, the data stream or signal sequence can be configured to be transmitted over a data communications connection, for example over the Internet.

Another embodiment includes a processing means, for example a computer or a programmable logic device, configured or adapted to perform any of the methods described herein.

A further embodiment comprises a computer on which the computer program for carrying out one of the methods described herein is installed.

Another embodiment according to the invention comprises a device or system configured to transmit a computer program for carrying out one of the methods described herein to a recipient. The receiver may be, for example, a computer, a mobile device, a storage device or the like. The device or system may, for example, comprise a file server for transmitting the computer program to the recipient.

The invention claimed is:

1. A computer-implemented method for determining the stability of substances or substance mixtures, the method comprising the following steps:

a data acquisition step in which a computer program receives raw and/or metadata for multiple product candidates, each product candidate comprises a starting value measurement data set and at least one further measurement data set, the starting value measurement data set and each measurement data set of the at least one further measurement data set representing a respective chemical profile of a respective substance or substance mixture of the respective product candidate, wherein the data acquisition step comprises obtaining, for each product candidate, the at least one further measurement data set by performing one or more of the following measurements on the product candidate: middle infrared spectroscopy, near infrared spectroscopy, UV/VIS spectroscopy, Raman spectroscopy, liquid chromatography, high performance liquid chromatography, ultra high performance liquid chromatography, gas chromatography, and/or mass spectrometry;

a data evaluation step comprising for each further measurement data set:

determining, by the computer program, the starting value measurement data set of the respective substance or substance mixture on the basis of raw and/or metadata of the starting value measurement data set; and quantifying, by the computer program, a change in the respective substance or substance mixture over time with respect to the starting value measurement data set and the at least one further measurement data set by means of a mathematical distance measure, wherein the mathematical distance measure is selectable by a user and wherein the user can select multiple mathematical distance measures for the quantification of the change in the respective substance or substance mixture, wherein the quantification of the change in the respective substance or substance mixture is performed on the basis of each selected mathematical distance measure; and performing, by the computer program, an additional qualitative analysis for the at least one further measurement data set, which is not included in the quantification of the change by means of the mathematical distance measure and produces distance values; and a data output step in which the computer program graphically displays the change in the respective substance or substance mixture for each further measurement data set, wherein the data output step comprises:

displaying the change in the respective substance or substance mixture as a box plot; and displaying the result of the additional qualitative analysis;

determining, by the computer program, a time at which the distance values reach a plateau value by fitting a kinetic curve to the distance values, wherein the plateau is indicated by asymptotic approximation of the calculated distance values; and outputting an indication that a process can be terminated based on the determined time at which the distance values reach the plateau value.

2. The method of claim 1, further comprising:

training a machine learning model using at least one of unsupervised or supervised machine learning; and wherein the data evaluation step comprises, for each further measurement data set, using the machine learning model to evaluate the further measurement data set.

3. The method of claim 1, wherein the at least one further measurement data set comprises at least one of:

data obtained by UV/VIS spectroscopy;

data obtained by Raman spectroscopy;

a (U) HPLC fingerprint;

a GC fingerprint;

a peak table from a chromatographic procedure;

at least one physical, biological or chemical parameter.

4. The method of claim 1, wherein the quantification of the change in the respective substance or substance mixture is based on a totality of the ingredients of the respective substance or substance mixture.

5. The method of claim 1, wherein the mathematical distance measure is selected from the following group: Euclidean distance, Mahalanobis distance, Manhattan distance, Pearson distance and/or Gower distance.

6. The method of claim 1, further comprising: a data preprocessing step comprising:

performing a stray light correction of the at least one further measurement data set;

carrying out a centering, normalization and/or scaling of the at least one further measurement data set; and/or performing a principal component analysis.

7. The method of claim 1, wherein the data output step comprises:

displaying means, medians, 0.25/0.75 quantiles, dispersion measures, highlighting possible outlier candidates; and/or performing at least one statistical test.

8. The method of claim 1, wherein the substance or substance mixture comprises solid and/or liquid and/or gaseous substances.

9. The method of claim 1, wherein the substance or substance mixture comprises biological, chemical, plant, animal, human substances or mixtures of substances, pharmaceutical compositions, plant medicinal products, chemical and/or biological medicinal products, cells, cell therapeutics, blood, blood products, organs, medicinal teas, verbena extract, thyme, rosemary and chamomile medicinal drug mixtures as an ethanolic extract or in powder form, drops, tablets, dragees, capsules, powders, granules, solutions, suspensions, juices, meat or minced meat, fruit juice, food supplements, cosmetics, emulsions, ointments and/or creams, as well as packaging, packaging materials, films, and/or polyvinyl chloride.

10. A non-transitory computer program product comprising instructions which, when executed by a computer, cause the computer to carry out the method of claim 1.

11. A device comprising means for carrying out the method of claim 1.

* * * * *